US010266820B2

(12) United States Patent
Ahn et al.

(10) Patent No.: US 10,266,820 B2
(45) Date of Patent: Apr. 23, 2019

(54) RNA/DNA NANOPARTICLE FOR SIRNA TARGET-SPECIFIC DELIVERY AND VEHICLE INCLUDING THE SAME

(71) Applicant: KOREA INSTITUTE OF SCIENCE AND TECHNOLOGY, Seoul (KR)

(72) Inventors: Hyung Jun Ahn, Seoul (KR); Ick Chan Kwon, Seoul (KR); Mihue Jang, Seoul (KR); Jong Hwan Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 573 days.

(21) Appl. No.: 14/754,556

(22) Filed: Jun. 29, 2015

(65) Prior Publication Data
US 2016/0208245 A1  Jul. 21, 2016

(30) Foreign Application Priority Data

Jan. 21, 2015  (KR) .................. 10-2015-0009729

(51) Int. Cl.
*C12N 15/11* (2006.01)
(52) U.S. Cl.
CPC ........ *C12N 15/111* (2013.01); *C12N 2310/14* (2013.01); *C12N 2310/3515* (2013.01); *C12N 2310/531* (2013.01); *C12N 2320/32* (2013.01)
(58) Field of Classification Search
None
See application file for complete search history.

(56) References Cited

U.S. PATENT DOCUMENTS

| 2009/0280058 A1 | 11/2009 | Tory et al. |
| 2013/0034599 A1* | 2/2013 | Thaxton ................. A61K 9/127 424/450 |

FOREIGN PATENT DOCUMENTS

| EP | 2 037 940 B1 | 3/2008 |
| KR | 1020100122405 A | 11/2010 |
| KR | 10-2011-0050338 A | 5/2011 |
| WO | WO 2008/124165 A2 | 10/2008 |

OTHER PUBLICATIONS

Lee et al, Molecularly self-assembled nucleic acid nanoparticles for targeted in vivo siRNA delivery, 2012, Nature Nanotechnology, 7: 389-393.*
Chaltin et al, Delivery of Antisense Oligonucleotides Using Cholesterol-Modified Sense Dendrimers and Cationic LipidsBioconjugate Chemistry, 2005, Bioconjugate Chemistry, 16: 827-836.*
Choi et al, Self-assembled amphiphilic DNA-cholesterol/DNA-peptide hybrid duplexes with liposome-like structure for doxorubicin delivery, 2013, Biomaterials, 34: 4183-4190.*
Park et al., The Korean Institute of Chemical Engineers, 2014, pp. 566-572, NICE vol. 32, No. 5.
Doh et al. Application of polysaccharides for surface modification of nanomedicines. Therapeutic Delivery, Dec. 2012, pp. 1447-1456, vol. 3, No. 12.
Lee et al. Self-assembled RNA interference microsponges for efficient siRNA delivery, Nature Materials , Apr. 2012, pp. 316-322 with Supplementary information.pp. 1-21, vol. 11 ,Letters, USA.
Oh et al. siRNA delivery systems for cancer treatment, Advanced Drug Delivery Reviews 61 , May 5, 2009, pp. 850-862, Elsevier, Korea.
Irena Melnikova, RNA-based therapies, Nature reviews drug discovery, Nov. 2007, pp. 863-864. vol. 6., USA.
Lee et al. Small-Interfering RNA (siRNA)-Based Functional Micro- and Nanostructures for Efficient and Selective Gene Silencing, Accounts of chemical research, Mar. 13, 2012, pp. 1014-1025, vol. 45, No. 7, Korea.
Cho et al. Low Molecular Weight PEI Conjugated Pluronic Copolymer: Useful Additive for Enhancing Gene Transfection Efficiency, Macromolecular Research, 2006, pp. 348-353 vol. 14, No. 3, Korea.
Choi et al. Polyethylene glycol-grafted poly-L-lysine as polymeric gene carrier, Journal of Controlled Release 54 ,1998, pp. 39-48, Elsevier, USA.
M. Zuker, Mfold web server for nucleic folding and hybridization prediction., Nucleic Acids Res. res. (31) (13), 3406-15 , 2003: RNA mfold program, http://mfold. ma. albany.edu/?q=mfold/RNA-Folding-Form.

(Continued)

*Primary Examiner* — Ekaterina Poliakova-Georgantas
(74) *Attorney, Agent, or Firm* — Goldilocks Zone IP Law

(57) ABSTRACT

A RNA/DNA nanoparticle for delivering siRNA where a RNA transcript including at least one hairpin structure hybridizes DNA-cholesterol conjugate and folate-DNA conjugate including a complementary sequence to the RNA transcript, and a composition including the RNA/DNA nanoparticle is provided. More specifically, because various siRNA used for different applications can be contained in the RNA/DNA nanoparticle for delivering siRNA at a high loading efficiency, and has stability to the outer attacks such as nuclease degradation. The RNA/DNA nanoparticle siRNA can be prepared by self-assembly without using polycationic agent which is harmful agent for body. The folate targeting to various cancer cells can accumulate the nanoparticle selectively on target cancer cell after intravenous injection, and make excellent gene-silencing effect inside the cancer tissue, thereby being used as a good agent for treating cancers.

8 Claims, 32 Drawing Sheets
(19 of 32 Drawing Sheet(s) Filed in Color)
Specification includes a Sequence Listing.

(56) References Cited

OTHER PUBLICATIONS

Park et al., the Korean institute of Chemical Engineers, Oct. 2014, pp. 566-572, NICE vol. 32, No. 5.
Calarco et al., The genotoxicity of PEI-based nanoparticles is reduced by acetylation of polyethylenimine amines in human primary cells, Jan. 4, 2013, pp. 10-17, Toxicology Letters, 218 (2013), Elsevier.

* cited by examiner

[Fig. 1a]
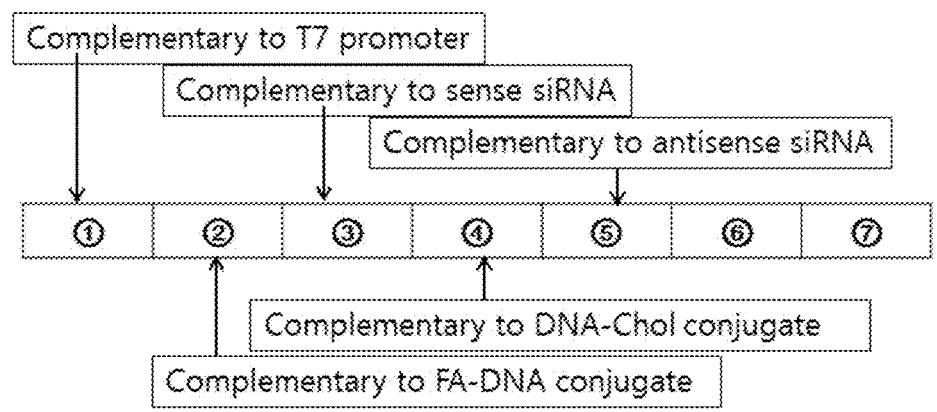
Sequence ID NO:1
① ATAGTGAGTCGTATTA
② ACGTACCAACAAGA
③ GAGTTCAAGTCCATCTACA
④ ATCTAAAAGTGGTGGGTGTGACCCTAAAA
⑤ TGTAGATGGACTTGAACTC
⑥ TTTAGAGGCAT
⑦ ATCCCT

[Fig. 1b]
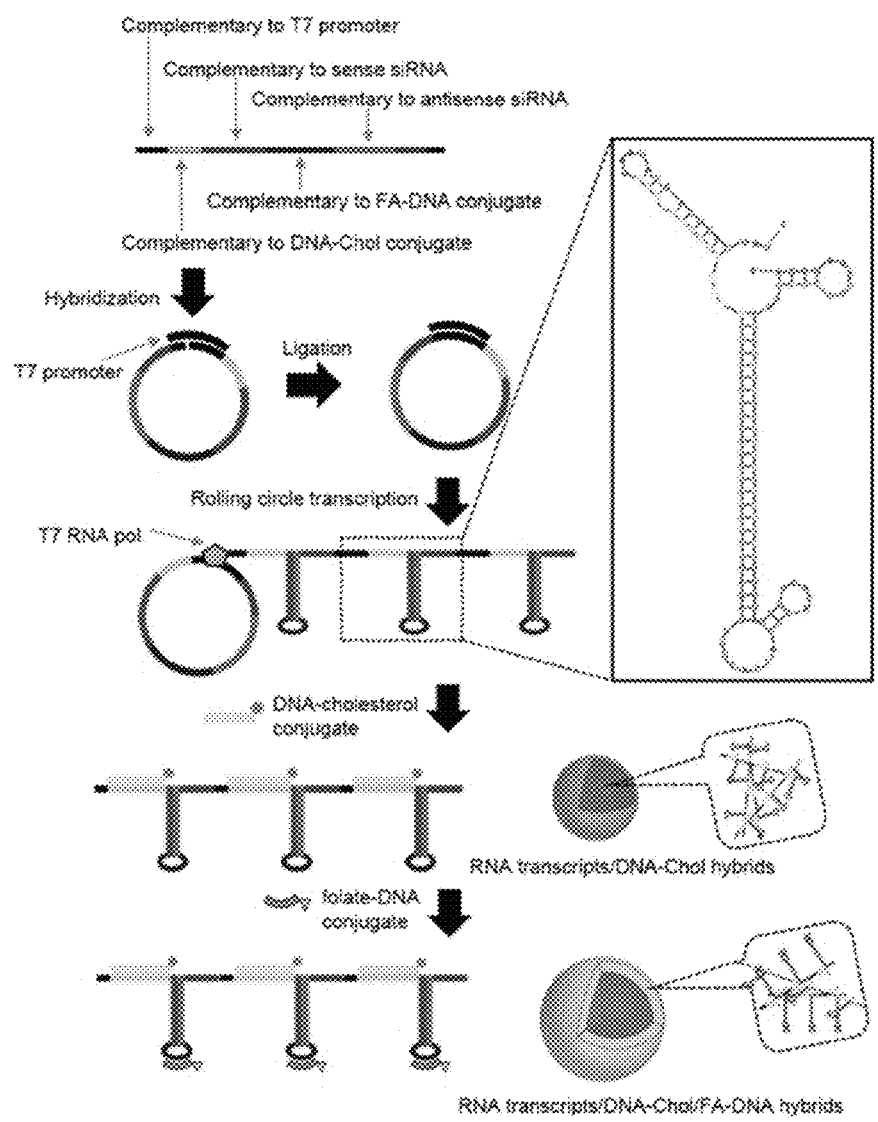

[Fig. 2a]
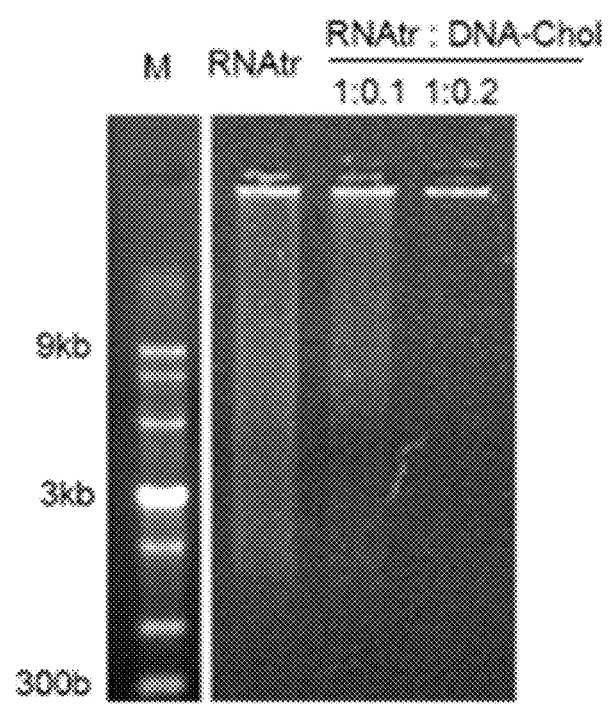

[Fig. 2b]
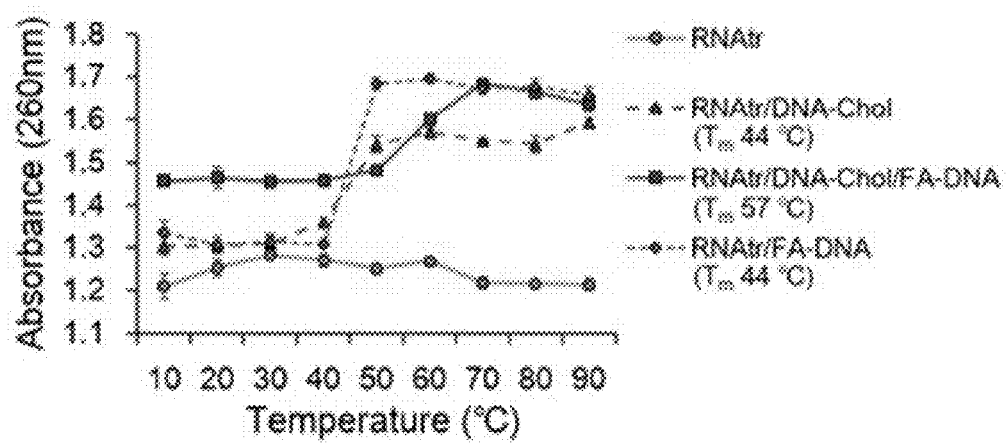

[Fig. 2c]
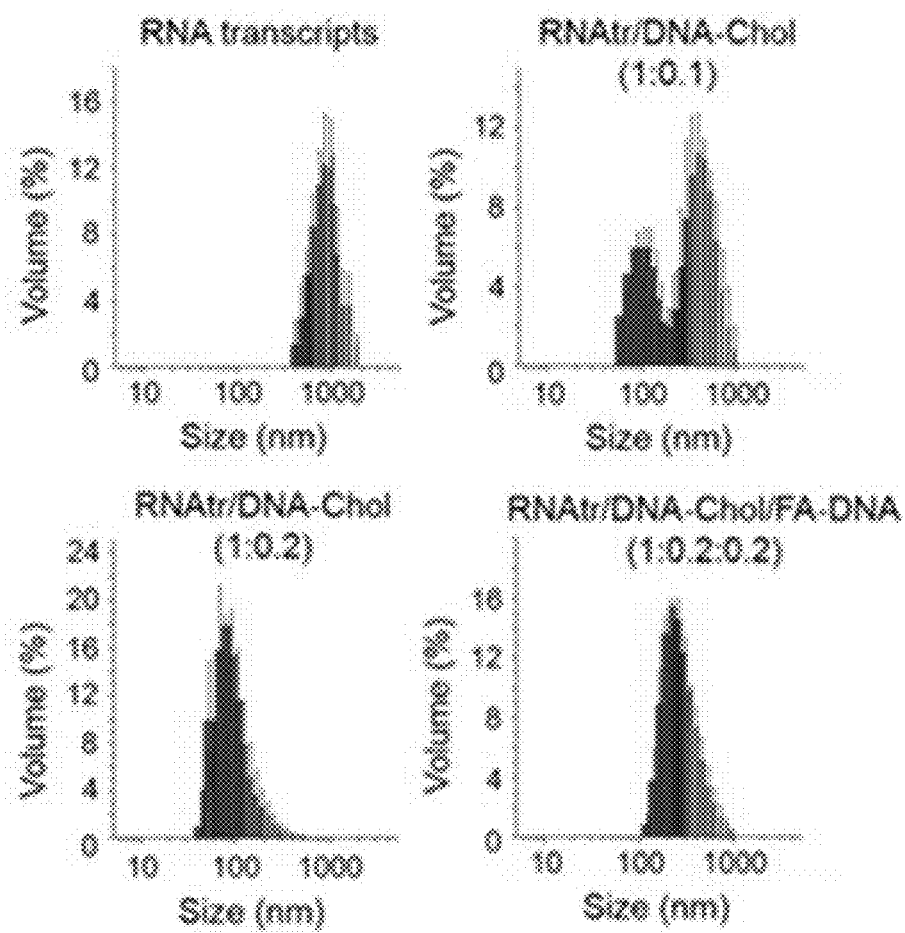

[Fig. 2d]
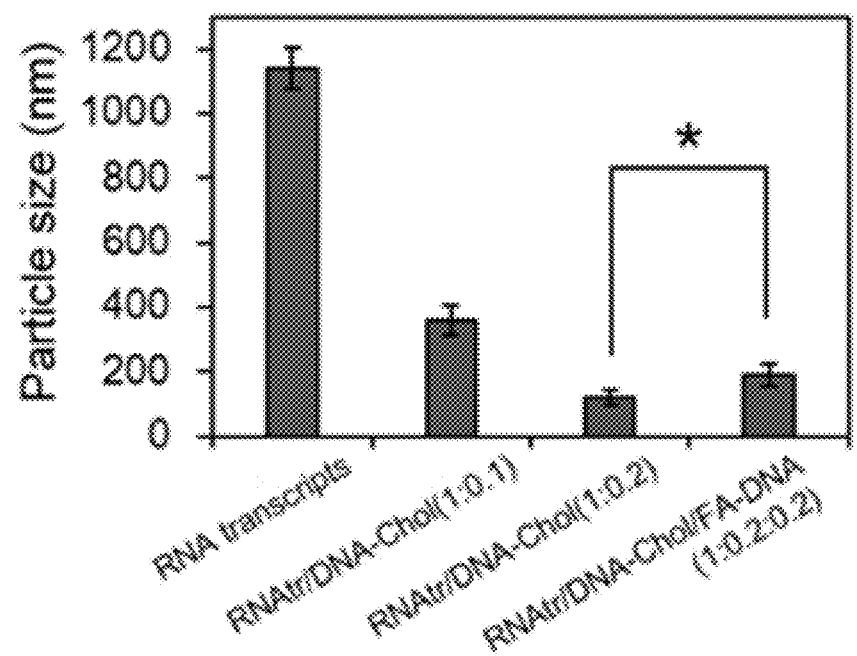

[Fig. 2e]
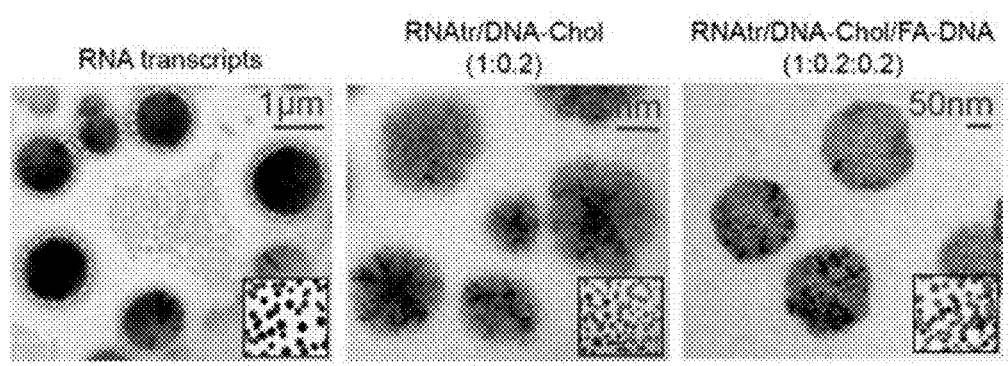

[Fig. 3a]
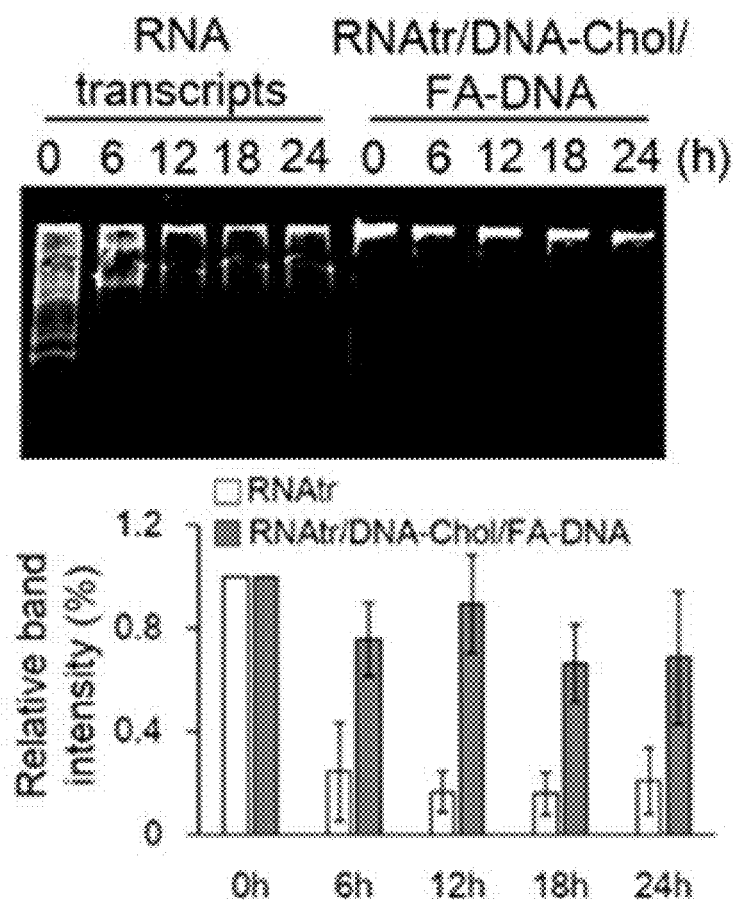

[Fig. 3b]
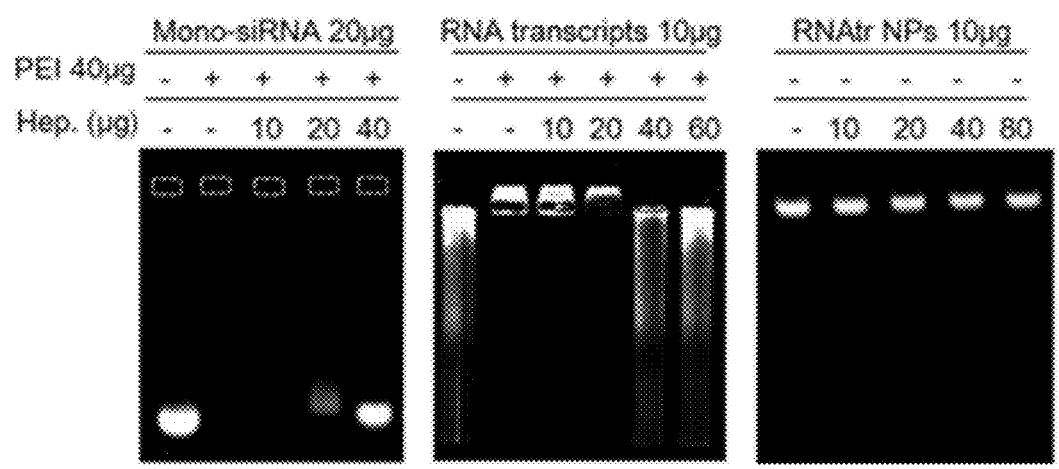

[Fig. 3c]
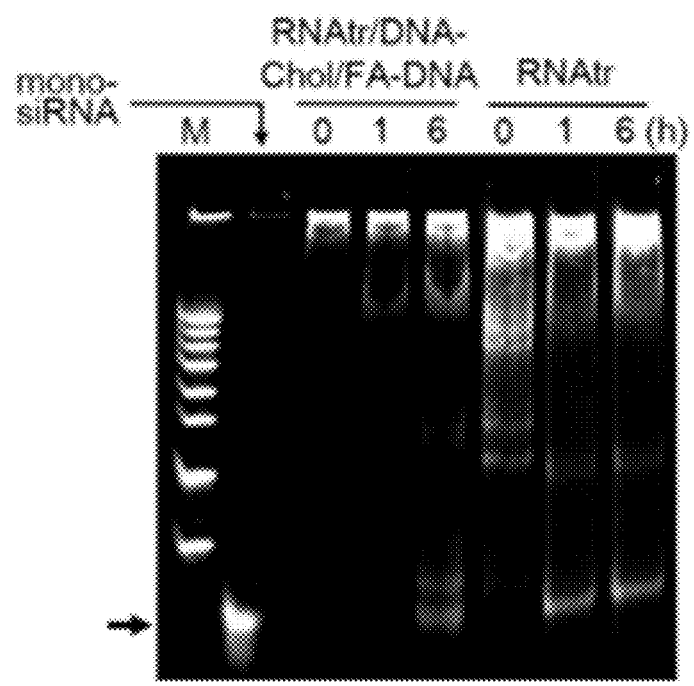

[Fig. 3d]
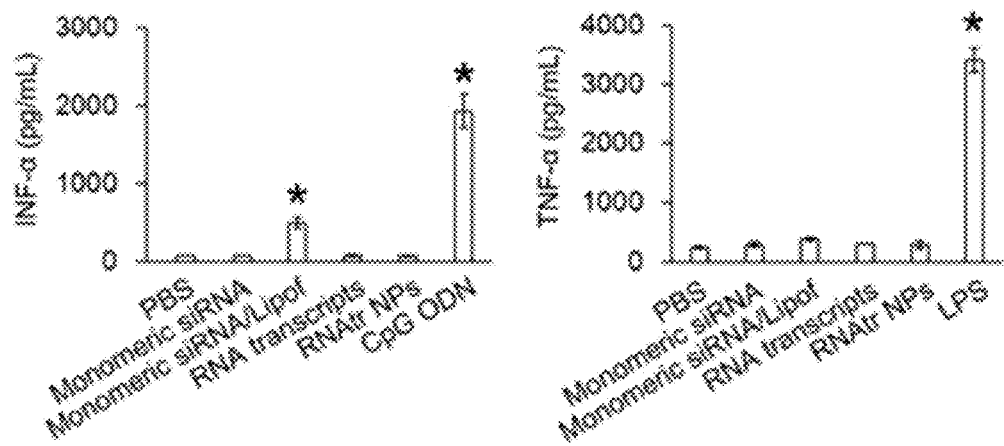

[Fig. 3e]
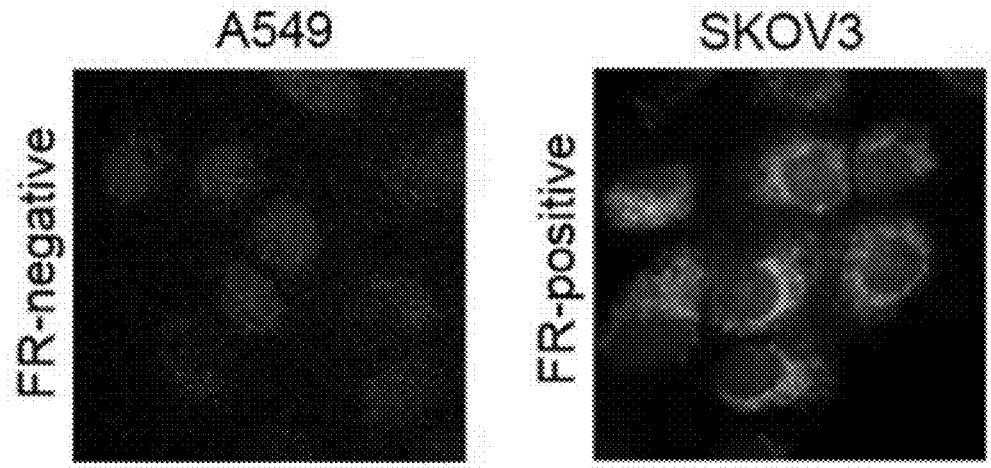

[Fig. 3f]
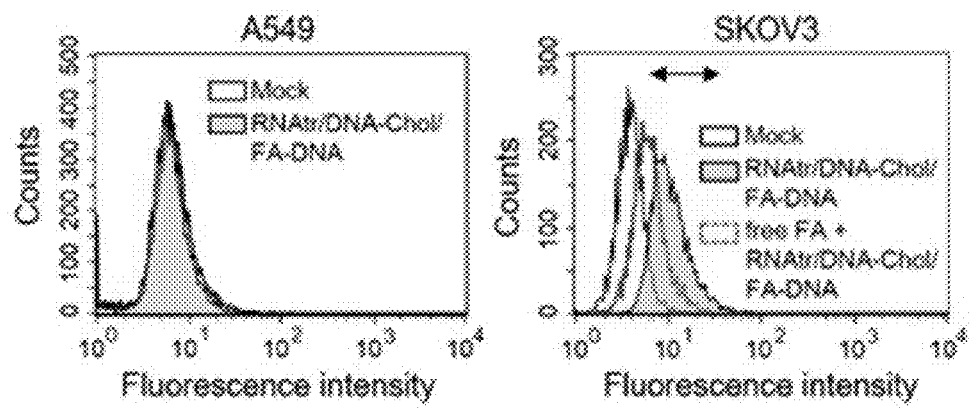

[Fig. 3g]
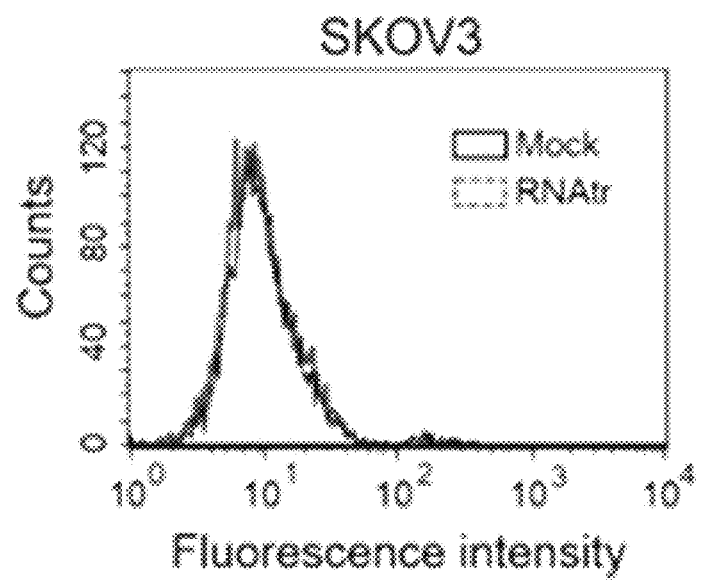

[Fig. 4a]
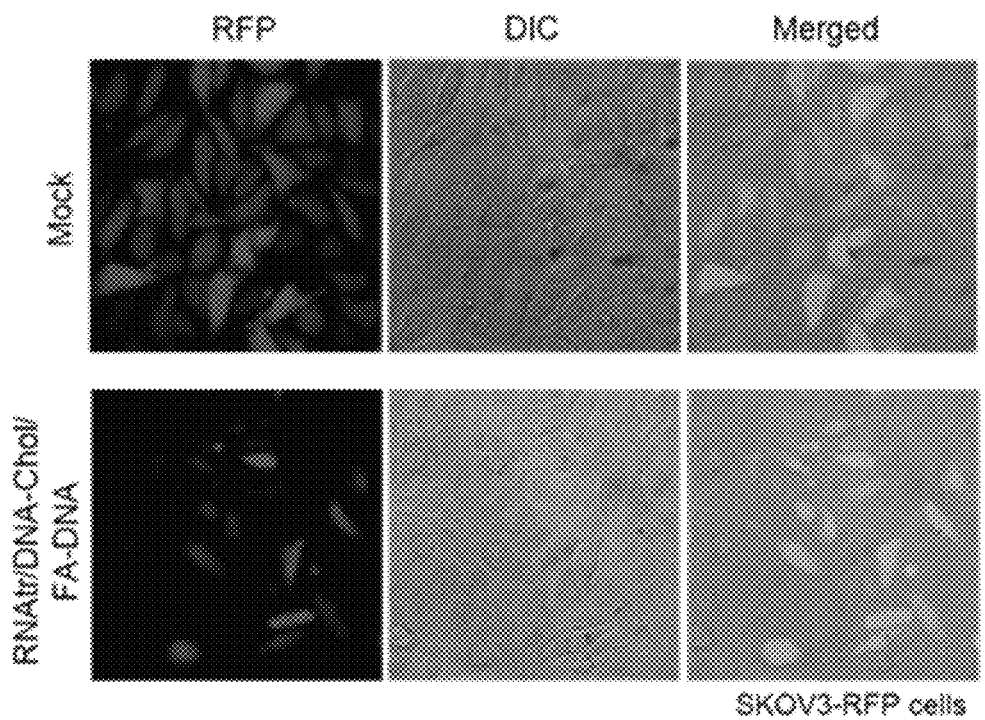

[Fig. 4b]
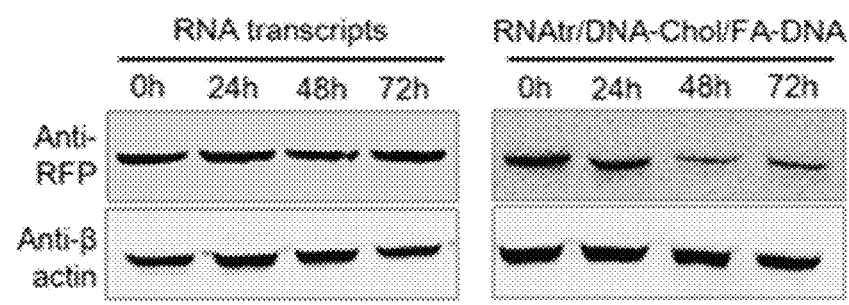

[Fig. 4c]
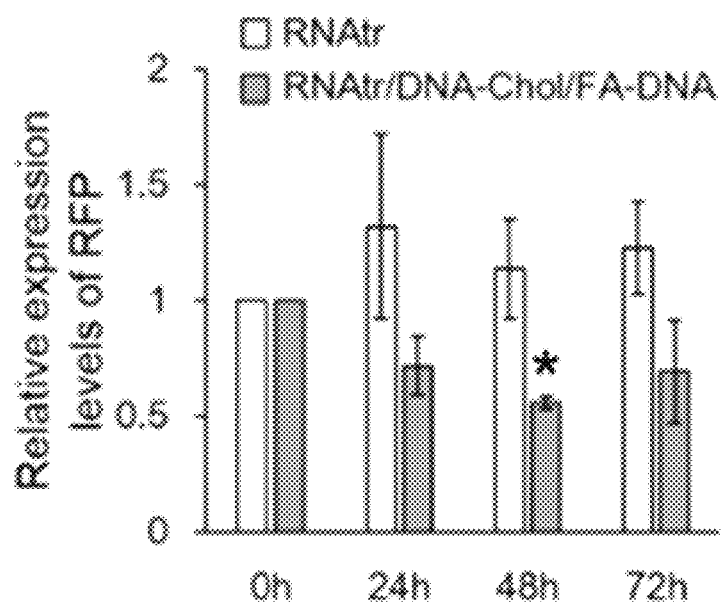

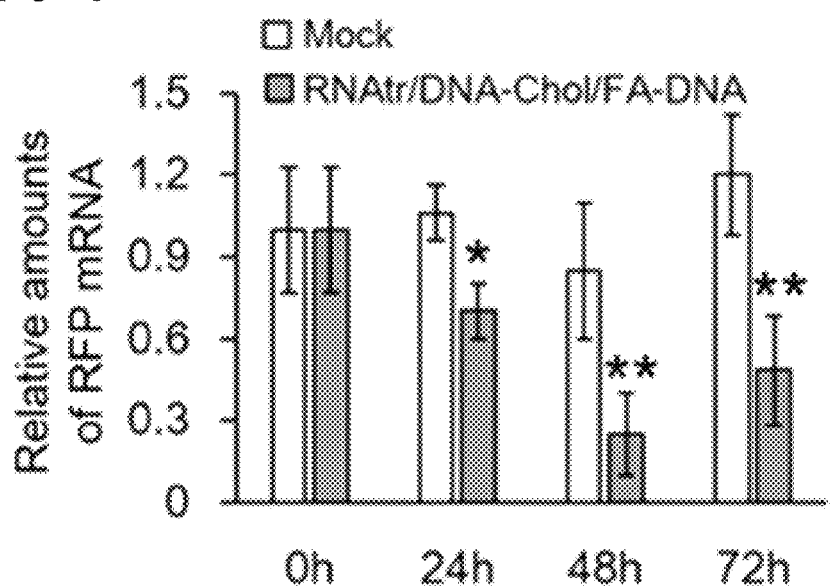
[Fig. 4d]

[Fig. 4e]
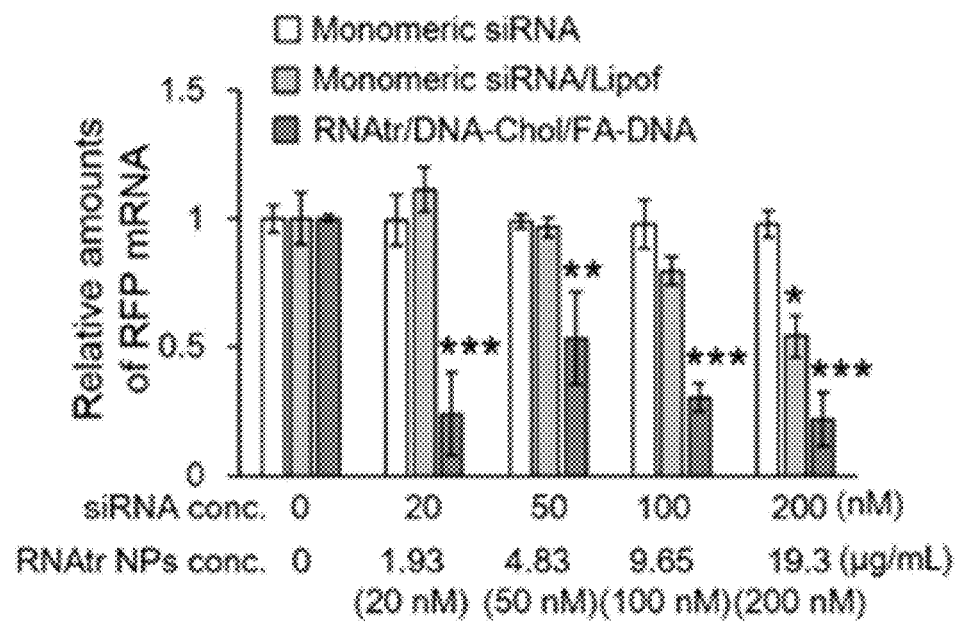

[Fig. 5a]
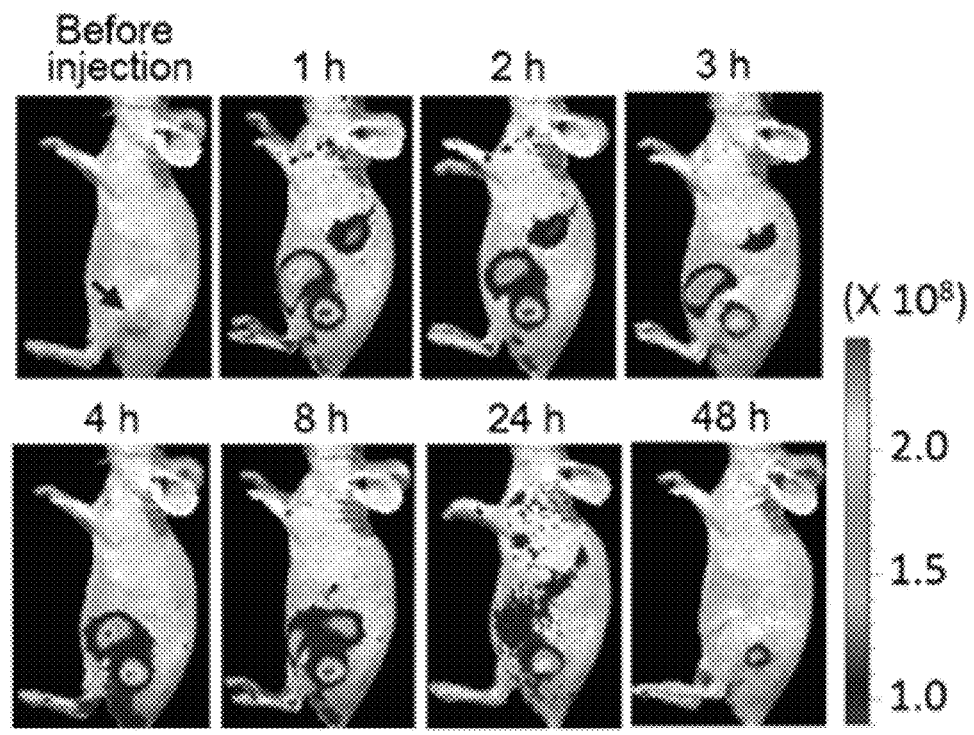

[Fig. 5b]
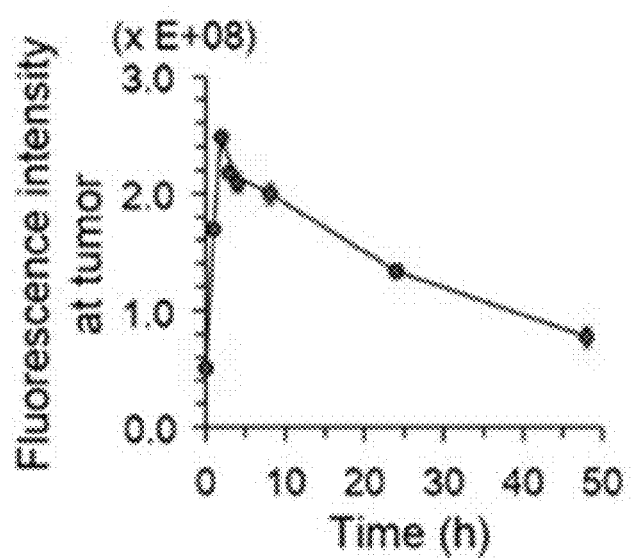

[Fig. 5c]
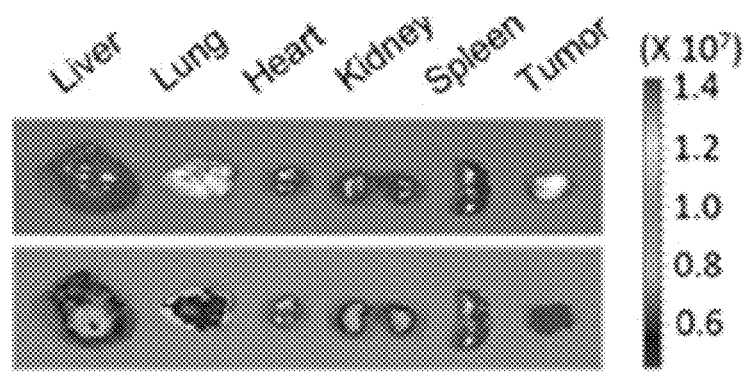

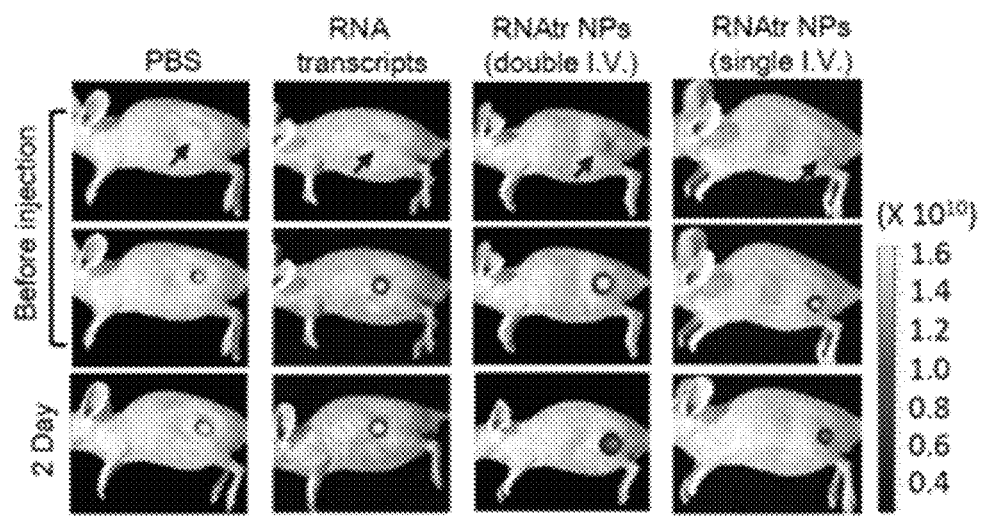
[Fig. 5d]

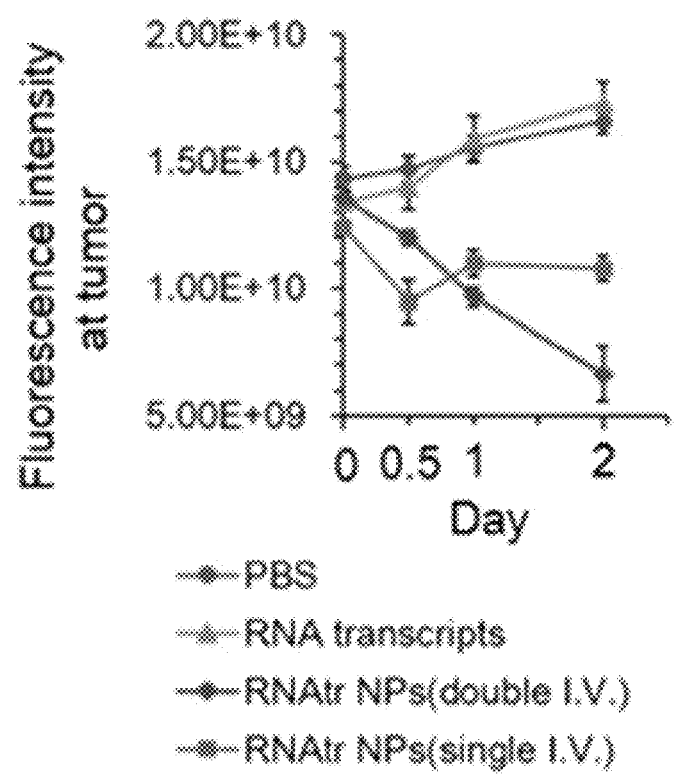
[Fig. 5e]

[Fig. 5f]
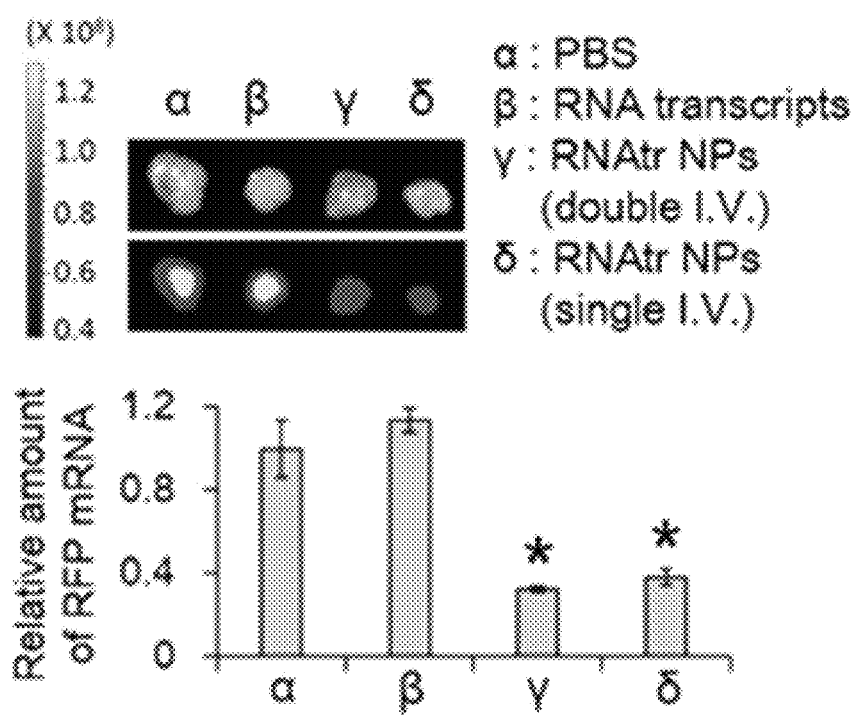

[Fig. 6a]
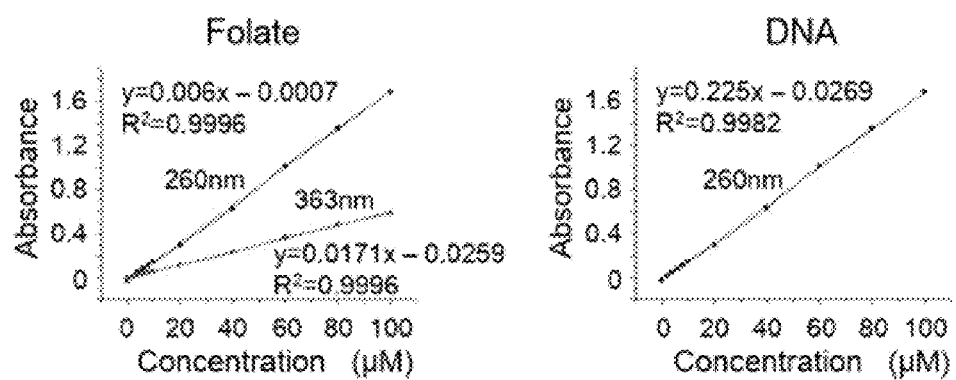

[Fig. 6b]
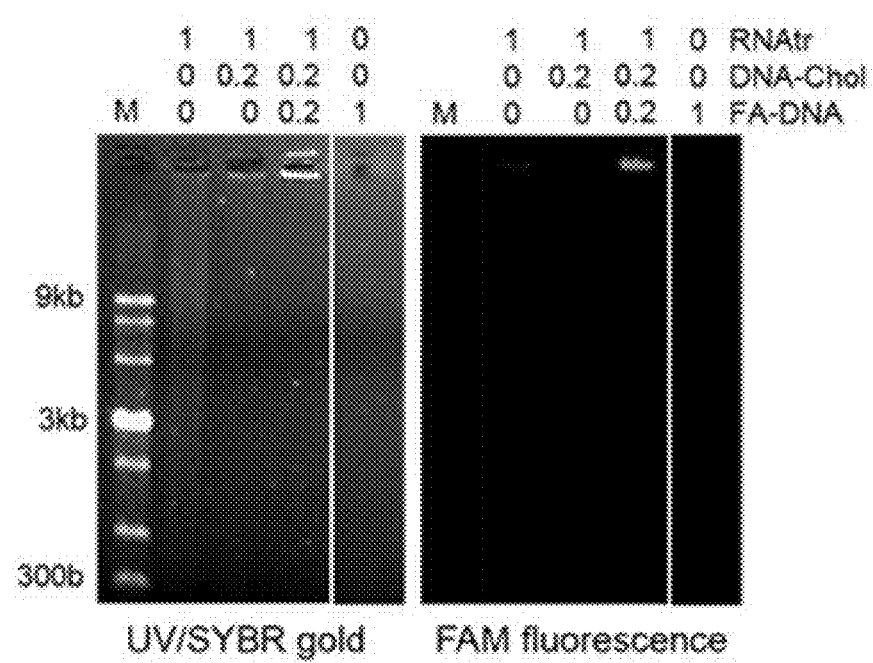

[Fig. 6c]
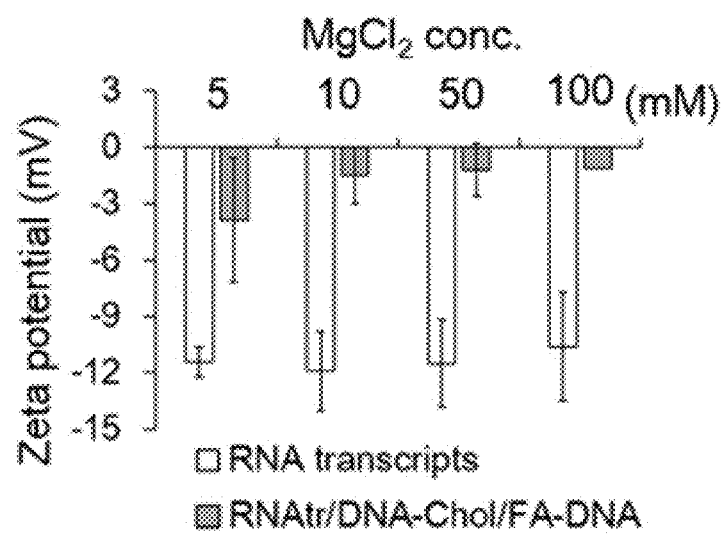

[Fig. 6d]
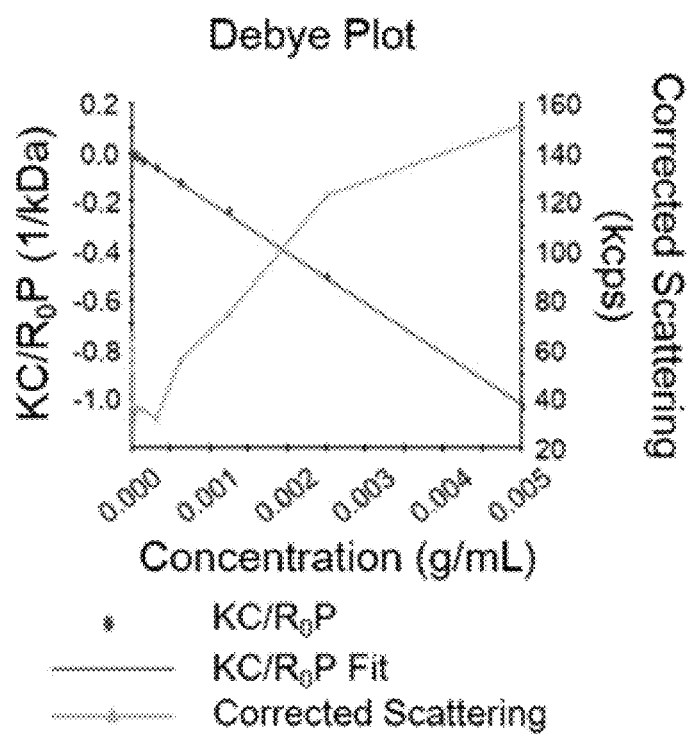

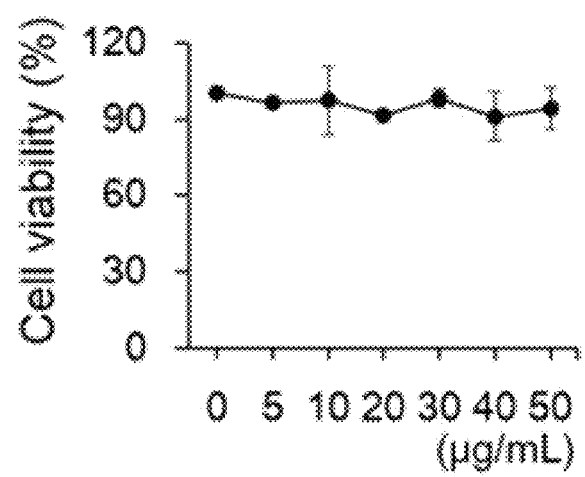
[Fig. 6e]

[Fig. 7]
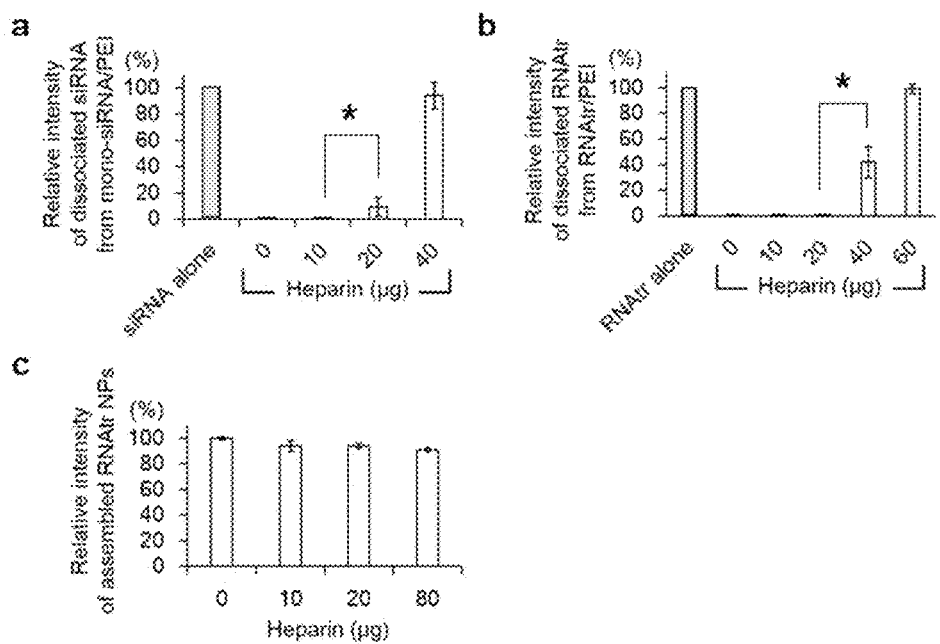

[Fig. 8]
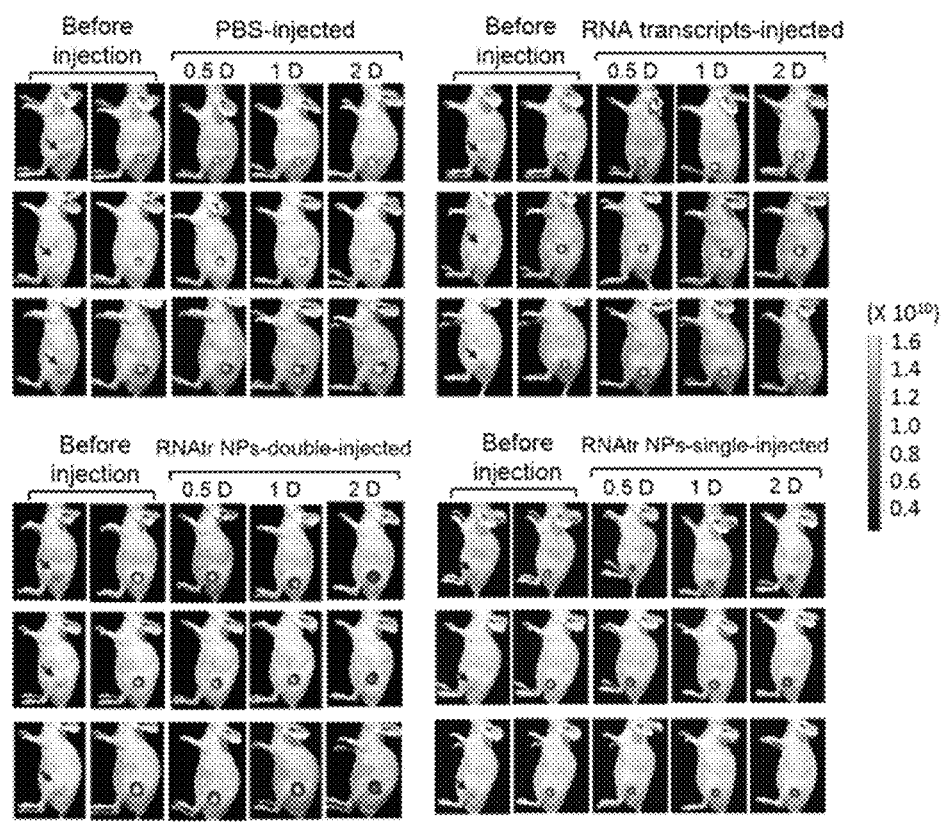

SEQUENCE LISTING

```
<160> NUMBER OF SEQ ID NOS: 5

<210> SEQ ID NO 1
<211> LENGTH: 114
<212> TYPE: DNA
<213> ORGANISM: Artificial Sequence
<220> FEATURE:
```

<223> OTHER INFORMATION: DNA Sequence corresponding to the RNA
      transcript including siRNA of interest

<400> SEQUENCE: 1
atagtgagtc gtattaacgt accaacaaga gagttcaagt ccatctacaa tctaaaagtg      60
gtgggtgtga ccctaaaatg tagatggact tgaactcttt agaggcatat ccct            114

<210> SEQ ID NO 2
<211> LENGTH: 30
<212> TYPE: DNA
<213> ORGANISM: Artificial Sequence
<220> FEATURE:
<223> OTHER INFORMATION: DNA sequence of DNA-cholesterol conjugate

<400> SEQUENCE: 2
atagtgagtc gtattaacgt accaacaaga                                       30

<210> SEQ ID NO 3
<211> LENGTH: 29
<212> TYPE: DNA
<213> ORGANISM: Artificial Sequence
<220> FEATURE:
<223> OTHER INFORMATION: DNA sequence of folate-DNA conjugate

<400> SEQUENCE: 3
atctaaaagt ggtgggtgtg accctaaaa                                        29

<210> SEQ ID NO 4
<211> LENGTH: 22
<212> TYPE: DNA
<213> ORGANISM: Artificial Sequence
<220> FEATURE:
<223> OTHER INFORMATION: T7 promoter

<400> SEQUENCE: 4
taatacgact cactataggg at                                               22

<210> SEQ ID NO 5
<211> LENGTH: 114
<212> TYPE: RNA
<213> ORGANISM: Artificial Sequence
<220> FEATURE:
<223> OTHER INFORMATION: RNA transcript including siRNA of interest

<400> SEQUENCE: 5
agggauaugc cucuaaagag uucaagucca ucuacauuuu agggucacac ccaccacuuu      60
uagauuguag auggacuuga acucucuugu ugguacguua auacgacuca cuau            114

RNA/DNA NANOPARTICLE FOR SIRNA TARGET-SPECIFIC DELIVERY AND VEHICLE INCLUDING THE SAME

CROSS REFERENCE TO RELATED APPLICATION

This application claims the benefit of Korean Patent Application No. 10-2015-0009729 on Jan. 21, 2015 with the Korean Intellectual Property Office, the disclosure of which is herein incorporated by reference in its entirety.

TECHNICAL FIELD

The present invention relates to an amphiphilic RNA/DNA nanoparticle which includes an RNA transcript containing siRNA for target delivery, a DNA-cholesterol conjugate, and a folate-DNA conjugate, and use thereof. More particularly, the present invention relates to a nanoparticle formed by complementary RNA/DNA base-pairing between the RNA transcript containing various siRNAs, and the DNA-cholesterol conjugate and the folate-DNA conjugate, in which this nanoparticle is used to secure stability against external attacks such as various degradation enzymes and to secure target specific delivery of siRNA to various cells with high siRNA loading efficiency.

BACKGROUND ART

RNA interference (RNAi) refers to a phenomenon where a double stranded RNA consisting of a sense RNA having a homologous sequence with mRNA of a target gene and an antisense RNA having a complementary sequence therewith is introduced to cells so as to selectively induce degradation of mRNA of the target gene or to suppress expression of the target gene. RNAi was first found in nematodes, and at present, it is observed in various organisms including yeasts, insects, plants, and humans as a highly preserved biological phenomenon.

Small interference RNA (siRNA), as a material of inducing RNAi, refers to a short RNA double helical strand consisting of about 20 to 30 nucleotides. Introduction of siRNA into cells enables to target mRNA of which the base sequence is complementary to the siRNA, thereby suppressing gene expression. Hence, siRNA has gained interest as an efficient means capable of controlling a life process to be a target by virtue of its therapeutic effects against diseases, easy preparation and high target selectivity.

Currently, cancers, virus infection diseases, autoimmune diseases, and neurodegenerative diseases have been studied as diseases to be treated by use of siRNAs, and their potentials as therapeutic agents for age-related macular degeneration (Bevasiranib; Opko Health, Inc., Miami, Fla., USA; clinical phase III) and respiratory syncytial virus infection (ALN-RSV01; Alnylam, Cambridge, Mass., USA; clinical phase II) have been reported as clinical trials thereof (Melnikova I. Nat Rev Drug Discov 2007, 6, 863-864). Furthermore, it was reported that a delivery system of siRNAs in human cancer therapy is possible by using cyclodextrin-based nanoparticle polymers having transferrin as their target (CALAA-01; Calando Pharmaceuticals, Pasadena, Calif., USA; clinical phase I) (Oh Y K. et al., Adv Drug Deliver Rev 2009, 61, 850-862).

However, siRNAs are in vivo degraded within a short time due to their low stability and the anionic nature thereof hinders them from readily penetrating cell membranes with the same negative charge, leading to low transmissibility into cells, and thus there is a demand for a technology of preparing vehicles for efficient intracellular delivery. Accordingly, in order to efficiently deliver siRNAs into cells, there is needed an effective novel delivery system that has resistance against degradation enzymes, circulates in the living body for a long time, reaches target cells via a clinically available injection route, and enables an effective cytoplasm release after cell penetration.

As existing siRNA delivery vehicles, recombinant plasmids or viral vectors of expressing siRNA have been used, or lipofectin, lipofectamine, cellfectin, cationic phospholipid nanoparticle, cationic polymer, or liposome-based delivery vehicles have been usually used. However, viral delivery vehicles are restricted by the size of a gene to be delivered and they do not guarantee in vivo stability thereof because they might cause immune side effects due to the immunogenicity of the surface proteins of the viral vectors. Further, the delivery vehicles using cationic molecules or synthetic polymers have showed low intracellular delivery efficiency and had cytotoxicity problems which might be caused during intracellular gene delivery procedures.

The vehicles using cationic molecules or cationic synthetic polymers that have been most frequently reported exhibit excellent delivery efficiency of plasmid DNA, but have a problem of low intracellular delivery efficiency of siRNA due to the low anionic charge density and intrinsic rigid structure of siRNA having a relatively short length of 20-23 mer, compared to plasmid DNA (Lee S H. et al., Acc. Chem. Res. 2012, 45, 1014-1025). That is, when a bond between siRNA and the cationic polymer vehicle forms by cation-anion electrostatic interactions, the low anionic charge density and intrinsic rigid structure of siRNA hinder compact structure formation of siRNA/vehicle complex, leading to formation of loose siRNA/vehicle complex. Thus, the bound siRNA could be easily attacked by degradation enzymes or negatively charged proteins in the blood stream.

Further, cationic synthetic polymer vehicles destroy cell membrane or mitochondrial membrane during intracellular delivery of siRNA due to high cationic charge density and limited biocompatibility, thereby generating a problem of cytotoxicity causing cell necrosis or cell death (Cho K C. et al., Macromol. Res. 2006, 14, 348-353). In order to solve this toxicity problem, many trials have been conducted to prepare various novel cationic polymers having reduced toxicity or to develop cationic polymer vehicles having reduced toxicity by modifying the existing cationic polymers. However, there is a still problem of low intracellular delivery efficiency due to the low charge density and intrinsic rigid structure of siRNA.

DISCLOSURE

Technical Problem

An object of the present invention is to provide an RNA/DNA nanoparticle for siRNA delivery, in which this nanoparticle is prepared without using cationic synthetic polymers causing cytotoxicity, and is used to secure stability against external attacks such as various degradation enzymes and to secure target specific delivery with high siRNA loading efficiency, and a preparation method thereof.

Technical Solution

The present invention relates to a nanoparticle, which is formed by complementary RNA/DNA base-pairing between an RNA transcript containing siRNA to be delivered, and a DNA-cholesterol conjugate and a folate-DNA conjugate. Specifically, an aspect of the present invention relates to an amphiphilic RNA/DNA nanoparticle for siRNA delivery, including:

(a) an RNA transcript including a repeating unit consisting of a sense sequence and an antisense sequence of siRNA to be delivered, a first RNA sequence, and a second RNA sequence, (b) a first DNA sequence-cholesterol conjugate which may complementarily bind to the first RNA sequence and include cholesterol linked at the 3'-terminus, and (c) a second DNA sequence-ligand conjugate which may complementarily bind to the second RNA sequence and include a target-specific ligand linked at the 5'-terminus.

The nanoparticle may have a diameter of 1 to 1,000 nm, for example, 150 nm to 450 nm.

The repeating unit of the RNA transcript may further include a sequence complementary to a transcription promoter sequence linked to at least one of the 5'-terminus and the 3'-terminus. Two or more of the repeating unit of the RNA transcript may be linked.

The repeating unit of the RNA transcript includes a sense sequence of siRNA to be delivered, a first RNA sequence, an antisense sequence of siRNA to be delivered, and a second RNA sequence which are arranged sequentially in the direction from the 5'-terminus to the 3'-terminus. The repeating unit of the RNA transcript may further include a sequence complementary to a transcription promoter sequence linked to at least one of the 5'-terminus and the 3'-terminus.

In the nanoparticle, the repeating unit of the RNA transcript forms a hairpin structure by complementary base-pairing between the sense and antisense sequences of siRNA to be delivered, and the first DNA sequence-cholesterol conjugate and the second DNA sequence-ligand conjugate may complementarily bind to the RNA transcript. The RNA transcript, the first DNA sequence-cholesterol conjugate, and the second DNA sequence-ligand conjugate may form nanoparticles by self-assembly in an aqueous solution.

The sense sequence and the antisense sequence of siRNA may be composed of 5 to 50 bases.

The first RNA sequence and the second RNA sequence may be composed of 5 to 50 bases. The ligand binding to the second RNA sequence may be a ligand specific to a target cell to which siRNA is delivered. For example, if the target cell is a cancer cell, a target-specific ligand means a cancer cell, cancer stem cell, or cancer marker-specific ligand, which is a cancer-specific binding component providing target specificity. The cancer targeting ligand may be a compound such as folate, a cancer targeting peptide such as RGD (Arg-Gly-Asp) peptide, a cancer targeting aptamer, or a cancer targeting antibody.

Another aspect of the present invention relates to a method of preparing the amphiphilic RNA/DNA nanoparticle for siRNA delivery, including:

preparing a DNA fragment complementary to the RNA transcript which includes the repeating unit consisting of the sense and antisense sequences of siRNA to be delivered, the first RNA sequence, and the second RNA sequence, and a sequence complementary to the transcription promoter sequence at both ends, ligating the DNA fragment and performing rolling circle transcription (RCT) using RNA polymerase to prepare the RNA transcript including one or more of the repeating unit, and forming nanoparticles in an aqueous solution by self-assembly of (a) the RNA transcript, (b) the first DNA sequence-cholesterol conjugate which may complementarily bind to the first RNA sequence and include cholesterol linked at the 3'-terminus, and (c) the second DNA sequence-ligand conjugate which may complementarily bind to the second RNA sequence and include a target-specific ligand linked at the 5'-terminus.

The present inventors improved the low delivery efficiency by using the polymerized RNA transcript, in which siRNAs are repeatedly linked by rolling circle transcription (RCT), as an siRNA vehicle.

The present invention provides an RNA/DNA hybrid nanoparticle for siRNA delivery, characterized in that the nanoparticle includes the RNA transcript having the repeated hairpin sequences containing siRNA, the DNA-cholesterol conjugate prepared by linking DNA complementary to a part of the RNA sequence with cholesterol, and the ligand-DNA conjugate prepared by linking DNA complementary to a part of the RNA sequence with a target-specific ligand, for example, folate, and the amphiphilic RNA/DNA hybrid formed by RNA/DNA hybridization forms a nanoparticle. Further, the present invention provides a method of preparing the RNA/DNA nanoparticle for siRNA delivery, including the step of forming the nanoparticle in an aqueous solution due to amphiphilic property of the RNAtr/DNA-Chol hybrid which is obtained from RNA/DNA base-pairing between complementary sequences.

The nanoparticle of the present invention is able to deliver siRNA to a specific target owing to its target-specific ligand. For example, if the target-specific ligand is folate, the nanoparticle is a target-specific vehicle capable of selectively delivering siRNAs to cancer cells overexpressing the folate receptor.

Hereinafter, the present invention will be described in more detail.

The present invention relates to an amphiphilic RNA/DNA nanoparticle for siRNA delivery, including:

(a) an RNA transcript including a repeating unit consisting of a sense sequence and an antisense sequence of siRNA to be delivered, a first RNA sequence, and a second RNA sequence, (b) a first DNA sequence-cholesterol conjugate which may complementarily bind to the first RNA sequence and include cholesterol linked at the 3'-terminus, and (c) a second DNA sequence-ligand conjugate which may complementarily bind to the second RNA sequence and include a target-specific ligand linked at the 5'-terminus.

All the existing siRNA vehicles have no target specificity, and thus there is a problem that they have only cell permeability without ability to discriminate cells. Under this background, the present inventors developed an RNA/DNA nanoparticle for siRNA delivery, in which an RNAtr/DNA-Chol/FA-DNA hybrid prepared via RNA/DNA hybridization between complementary sequences of RNAtr/DNA-Chol hybrid and folate-DNA (FA-DNA) conjugate exhibits cancer cell target specificity as well as cell permeability. Finally, they provided an RNA/DNA nanoparticle for siRNA delivery having the reduced risk of cytotoxicity and improved delivery efficiency, and a composition including the same so as to remarkably reduce cytotoxicity and to allow cancer cell-specific siRNA delivery.

The repeating unit of the RNA transcript includes a repeating unit consisting of sense and antisense sequences of siRNA to be delivered, a first RNA sequence, and a second RNA sequence, and the repeating unit may be repeated once or more, for example, 1 to 1,000,000, and more preferably 10 to 1,000 times.

The nanoparticle according to the present invention is an RNA/DNA nanoparticle formed by hybridization via RNA/

DNA base-pairing between the RNA transcript having repeated hairpin sequences containing siRNA, and the DNA-cholesterol conjugate and the folate-DNA conjugate having sequences complementary to the RNA transcript, in which the repeating unit of the RNA transcript forms a hairpin structure by complementary binding of the sense and antisense sequences of siRNA to be delivered, and the first DNA sequence-cholesterol conjugate and the second DNA sequence-ligand conjugate complementarily bind to the RNA transcript. The RNA transcript, first DNA sequence-cholesterol conjugate, and the second DNA sequence-ligand conjugate may form the nanoparticle by self-assembly in an aqueous solution.

The nanoparticle according to the present invention has the promising possibility as a cancer therapeutic agent, because the nanoparticle has high loading efficiency and secures stability against external attack such as various degradation enzymes, and it is formed by self-assembly without use of a polycationic agent having cytotoxicity, and selectively accumulated in the cancer tissue owing to folate targeting various cancer cells after intravenous injection so as to exhibit excellent gene silencing effects in the cancer tissue.

Since the RNA/DNA nanoparticle is a particle containing numerous repeats of siRNA sequences, it exhibits high siRNA loading efficiency capable of delivering siRNA of 20 to 50% by weight, for example, 24.4% by weight, based on the weight of the vehicle.

The repeated hairpin structures are formed, the repeated sense and antisense sequences of the red fluorescence protein (RFP)-targeting siRNA are included, and numerous repeats of the sequences complementary to the DNA-Chol conjugate and the folate-DNA conjugate are included.

The RNA hairpins of the nanoparticle are placed inside the RNA/DNA nanoparticle of the present invention, thereby being protected. Such RNA hairpins placed inside the RNA/DNA nanoparticle are physically blocked from the outside, and thus protected from degradation enzymes such as nuclease, thereby showing excellent stability. When this composition for siRNA delivery of the present invention is used, the recombinant protein for delivery exposes the target-specific folate to its outside and thus effectively binds to and permeates the target cell, and finally, the RNA hairpins are degraded into siRNAs by cytoplasmic Dicer enzymes, thereby effectively suppressing mRNA expression. Consequently, expression of a target gene containing a disease-associated gene is suppressed, and treatment of the disease is realized.

The repeating unit of the RNA transcript includes the sense sequence of siRNA to be delivered, the first RNA sequence, the antisense sequence of siRNA to be delivered, and the second RNA sequence which are arranged sequentially in the direction from the 5'-terminus to the 3'-terminus.

The repeating unit of the RNA transcript may further include a sequence complementary to a transcription promoter sequence linked to at least one of the 5'-terminus and the 3'-terminus. The promoter is introduced in order to perform preparation of the RNA transcript by insertion of the transcription promoter sequence. A schematic diagram of the repeating unit of the RNA transcript according to the present invention is shown in FIG. 1a.

A specific example of the RNA transcript according to the present invention may be an RNA sequence complementary to a DNA sequence of SEQ ID NO. 1, that is, an RNA sequence of SEQ ID NO. 5, but is not particularly limited thereto. Specifically, the RNA transcript may be prepared by including sense and antisense sequences of siRNA which is intended to be delivered by means of the nanoparticle. siRNA is not particularly limited, as long as it suppresses mRNA expression of a disease-associated gene to induce a therapeutic effect on the disease. It may include siRNA composed of 15 to 50 bases, for example, 19 to 30 bases.

Specifically, the linear DNA template represented by SEQ ID NO. 1 is subjected to rolling-circle transcription (RCT) using RNA polymerase so as to prepare the RNA transcript including the repeated RNA sequences of SEQ ID NO. 5. For example, if the transcription promoter is T7 transcription promoter, for example, having a nucleotide sequence of SEQ ID NO. 4, an RNA transcript synthesized by T7 RNA polymerase may be obtained. The linear DNA template may have a sequence complementary to T7 promoter sequence at its both ends, and the RNA transcript may form the repeated hairpin structures and include the repeated sense and antisense sequences of siRNA and numerous repeats of the sequences complementary to the DNA-Chol conjugate and the folate-DNA conjugate.

The first DNA sequence-cholesterol conjugate complementarily binds to the first RNA sequence and includes cholesterol linked at the 3'-terminus. In order to reduce the micrometer size of the RNA transcript (RNAtr) to a cell-permeable nanometer size, the DNA-cholesterol conjugate (DNA-Chol) is subjected to RNA/DNA hybridization therewith using a complementary sequence, and consequently, the amphiphilic RNAtr/DNA-Chol hybrid is prepared due to hydrophobic property of cholesterol. This RNA/DNA hybrid forms a nanometer-sized nanoparticle.

In the present invention, since the DNA-Chol conjugate includes cholesterol as a hydrophobic molecule, the RNAtr/DNA-Chol hybrid acquires the amphiphilic property and therefore, highly condensed nanoparticles are formed by self-assembly in an aqueous solution. Accordingly, when injected to the body, the particles may have high stability against attack of nuclease in the blood.

In an embodiment of the present invention, a sequence of the first DNA-Chol conjugate may be exemplified by SEQ ID NO. 2, but is not limited thereto, and the sequence may be properly prepared according to the sequence of the RNA transcript.

The second DNA sequence-ligand conjugate complementarily binds to the second RNA sequence and includes a target-specific ligand linked at the 5'-terminus. The ligand binding to the second RNA sequence may be a ligand specific to a target cell to which siRNA is intended to be delivered. For example, in the case of cancer cells, the target-specific ligand means a cancer cell, cancer stem cell, or cancer marker-specific ligand, which is a cancer-specific binding component providing target specificity. The cancer targeting ligand may be a compound such as folate, a cancer targeting peptide such as RGD (Arg-Gly-Asp) peptide, a cancer targeting aptamer, or a cancer targeting antibody. In the present invention, for example, the folate-DNA conjugate may improve deliverability to target cells, because of introduction of a folate receptor-targeting ligand, folate. Specifically, since the RNA/DNA nanoparticle for siRNA delivery exposes folate to its outside, folate binds to a folate receptor membrane protein which is specifically overexpressed on cancer cells, and therefore, the nanoparticle exhibits a cancer cell-specific targeting effect.

The first RNA sequence and the second RNA sequence may be composed of 5 to 50 bases.

In an embodiment of the present invention, the ligand-DNA conjugate having the sequence complementary to the RNA transcript may have a sequence represented by SEQ ID NO. 3, but is not limited thereto, and the sequence may be properly prepared according to the sequence of the RNA transcript. The folate-DNA conjugate having SEQ ID NO. 3 was prepared by EDC coupling of 5'-amine-modified DNA and folate (see Example 1-2).

The amphiphilic RNAtr/DNA-Chol/FA-DNA hybrid is prepared by complementary binding between the RNA transcript produced by RCT reaction and the DNA-cholesterol conjugate and the folate-DNA conjugate, and this RNA/DNA hybrid forms a nanometer-sized nanoparticle by self-assembly (see Example 2).

It was also confirmed that the RNA/DNA nanoparticles have excellent stability against nuclease attack under 30% serum conditions, and the structure of the RNA/DNA nanoparticle is not disassembled by charge-charge interaction between the nanoparticles and extracellular macroanionic biomaterials such as heparin (see Example 3). After internalization of the nanoparticles into cells, siRNAs are generated by Dicer enzymes (see Example 3), and cancer cell-specific delivery of RNA/DNA nanoparticles occurs depending on the presence of the folate receptor (see Example 4). Further, when the RNA/DNA nanoparticles are delivered to the cytoplasm, they cause silencing of the target gene (see Example 5). Thus, the RNA/DNA nanoparticles may be used as siRNA vehicles.

In another aspect, the present invention relates to a method of preparing the amphiphilic RNA/DNA nanoparticle for siRNA delivery, including the steps of: preparing (a) the RNA transcript including the repeating unit consisting of the sense and antisense sequences of siRNA to be delivered, the first RNA sequence, and the second RNA sequence, and forming nanoparticles in an aqueous solution by self-assembly of (a) the RNA transcript, (b) the first DNA sequence-cholesterol conjugate which may complementarily bind to the first RNA sequence and include cholesterol linked at the 3'-terminus, and (c) the second DNA sequence-ligand conjugate which may complementarily bind to the second RNA sequence and include a target-specific ligand linked at the 5'-terminus.

The (a) RNA transcript, (b) first DNA sequence-cholesterol conjugate, and (c) second DNA sequence-ligand conjugate are the same as described above.

The step of preparing the RNA transcript may be performed by preparing a DNA fragment complementary to the RNA transcript which includes the repeating unit consisting of the sense and antisense sequences of siRNA to be delivered, the first RNA sequence, and the second RNA sequence, and a sequence complementary to the transcription promoter sequence at both ends, ligating the DNA fragment, and then performing rolling circle transcription (RCT) using RNA polymerase to prepare the RNA transcript including one or more of the repeating unit. An example of the preparation method of the RNA transcript according to the present invention is illustrated in detail in FIGS. 2a-2e.

The present invention relates to a method of preparing the RNA/DNA nanoparticle for siRNA delivery, including the steps of preparing the RNAtr/DNA-Chol nanoparticle by hybridization of the RNA transcript having numerous repeats of the hairpin sequence containing the siRNA sequence and the hydrophobic DNA-Chol conjugate, and then preparing the RNAtr/DNA-Chol/FA-DNA nanoparticle by additional hybridization of the RNAtr/DNA-Chol nanoparticle and the folate-DNA conjugate.

An embodiment of the present invention provides a vehicle for target-specific siRNA delivery using the nanoparticle for siRNA delivery, and specifically, it may be an RNA/DNA nanoparticle for cancer-specific siRNA delivery, which includes the second DNA sequence-folate conjugate as the second DNA sequence-ligand conjugate.

Further, the present invention provides a therapeutic composition for siRNA-associated disease selected from the group consisting of cancers, age-related macular degeneration, virus infection diseases, autoimmune diseases, and neurodegenerative diseases, which is characterized in that the recombinant protein for siRNA delivery and siRNA are included, and the siRNA is located inside the recombinant protein.

The siRNA-associated disease may include, but is not limited to, any disease known to be treated by siRNAs, and preferably, the disease may be selected from the group consisting of cancers, age-related macular degeneration, virus infection diseases, autoimmune diseases, and neurodegenerative diseases. The cancers may include breast cancer, lung cancer, head and neck cancer, brain cancer, abdominal cancer, colon cancer, esophagus cancer, stomach cancer, gastric cancer, liver cancer, tongue cancer, neuroblastoma, osteosarcoma, ovarian cancer, pancreatic cancer, prostate cancer, Phillips' tumor, retinoblastoma, multiple myeloma, skin cancer, lymphoma and blood cancer, but are not limited thereto.

The therapeutic composition may be administered to mammals including humans via various routes, and it may be administered parenterally (e.g., intravenous, subcutaneous, intraperitoneal or local application) according to the methods to be intended, and the administration dosage may vary depending on conditions and weight of a patient, severity of disease, type of a drug, route and time of administration, but it may be suitably determined by those skilled in the pertinent art.

If the therapeutic composition according to the present invention is to be formulated, it may be prepared using a diluent or an excipient including a filler, an extender, a binder, a wetting agent, a disintegrating agent, and a surfactant which are normally used.

Solid formulations for oral administration may include a tablet, a pill, a powder, a granule, a capsule, a troche, etc. and such solid formulations are formulated by blending one or more compounds according to the present invention with one or more excipients, for example, starch, calcium carbonate, sucrose or lactose or gelatin. Furthermore, in addition to the simple excipient, lubricating agents such as magnesium stearate and talc are used. Liquid formulation for oral administration may include a suspension, a solution for internal use, an emulsion or a syrup, and in addition to water and liquid paraffin which are simple diluents frequently used, several excipients, for example, a wetting agent, a sweetening agent, a flavoring agent, a preservative, etc. may be included.

Formulations for parenteral administration may include a sterilized aqueous solution, a non-aqueous solvent, a suspension, an emulsion, a lyophilized formulation, a suppository, etc.

For the non-aqueous solvent or suspension, propylene glycol, polyethylene glycol, a vegetable oil such as olive oil, an injectable ester such as ethyl oleate, etc may be used. For the suppository base, witepsol, macrogol, tween 61, cacao butter, laurin butter, glycerol, or gelatin may be used.

The therapeutic composition according to the present invention is administered in a pharmaceutically effective amount. The "pharmaceutically effective amount", as used herein, refers to a sufficient amount to treat a disease at a reasonable benefit/risk ratio applicable for medical treatment, and an effective dose level may be determined by the type or severity of patient's disease, activity of a drug, sensitivity to a drug, administration time, administration route and excretion ratio, duration of treatment, and other drugs to be concurrently used, and other factors well known in the medical field. The therapeutic composition of the present invention may be administered as an individual therapeutic agent or in combination with other therapeutic agents. The composition may be administered sequentially or concurrently with existing therapeutic agents, or may be administered in a singular or multiple doses. It is important to administer the composition in the minimum amount that can exhibit the maximum effect without causing side effects, in view of all the above-described factors, and it can be easily determined by those skilled in the art.

In particular, the effective amount of the compound according to the present invention may vary depending on the age, gender and weight of a patient, and in general, 0.1 to 100 mg, preferably 0.5 to 10 mg per kg of body weight may be administered daily or on every other day, ranging from one to three times per day. However, since the amount may be increased or decreased in light of the route of administration, the severity of obesity, gender, weight, age, etc., it should be understood that the dosage suggested above does not limit the scope of the invention in any way.

Effect of the Invention

RNA/DNA nanoparticles for siRNA delivery of the present invention have excellent biocompatibility, because they secure siRNA stability against external attack such as various degradation enzymes, show very excellent siRNA loading efficiency, and deliver siRNA without using cytotoxic cationic condensing agents of the existing siRNA vehicles. Further, the nanoparticles are able to selectively deliver siRNAs to cancer cells and cancer tissues owing to target-specific folate which targets cancer cells. Accordingly, the nanoparticles of the present invention may be effectively used as siRNA delivery vehicles with improved in vivo stability for siRNA therapeutic agents, cell-based drug screening compositions and research.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1a is a schematic diagram showing a repeating unit of an RNA transcript according to the present invention, and FIG. 1b is a schematic illustration showing a generation process of RNA/DNA nanoparticles for siRNA delivery according to an embodiment of the present invention, in which a two-dimensional structure of siRNA-containing hairpin was analyzed by RNA mfold program (available in http://mfold.rna.albany.edu/?q=mfold/RNA-Folding-Form) (solid line box);

FIG. 2a shows the result of 3% agarose gel electrophoresis of an RNA transcript obtained by RCT and an RNA transcript/DNA-Chol hybrid (1:0.1, or 1:0.2, w/w), FIG. 2b shows the result of measuring absorbance of RNA transcript, RNA transcript/DNA-Chol hybrid (1:0.2, w/w), and RNA transcript/DNA-Chol/FA-DNA hybrid (1:0.2:0.2, w/w/w) at 260 nm over temperature, FIGS. 2c and 2d show the results of analyzing size distribution and average size of RNA transcript, RNA transcript/DNA-Chol hybrid (1:0.1 and 1:0.2, w/w), and RNA transcript/DNA-Chol/FA-DNA hybrid (1:0.2:0.2, w/w/w) using dynamic light scattering, the results are presented as mean±standard deviation (n=5), $*p<0.01$ by one-way ANOVA, and FIG. 2e shows the results of analyzing particle shape and size of RNA transcript, RNA transcript/DNA-Chol hybrid (1:0.2, w/w), and RNA transcript/DNA-Chol/FA-DNA hybrid (1:0.2:0.2, w/w/w) by transmission electron microscopy;

FIG. 3a shows stability against nuclease when RNA transcript and RNA transcript/DNA-Chol/FA-DNA hybrid were reacted under 30% fetal bovine serum (FBS) conditions, FIG. 3b shows stability of RNA transcript/DNA-Chol/FA-DNA nanoparticle under polyanionic conditions such as heparin found in the extracellular matrix, and also shows that siRNA is easily dissociated under heparin condition from monomeric siRNA/PEI complexes formed by charge-charge interaction, and also easily dissociated under heparin condition from RNA transcript/PEI complexes, FIG. 3c shows siRNA generation over time after treatment of RNA transcript and RNAtr nanoparticle with Dicer (1.5 unit), in which monomeric siRNA duplex is used as a control, FIG. 3d shows interferon-α release and TNF-α release by innate immune response at 24 hours after treatment of human peripheral blood mononuclear cells (PBMC) with various siRNA delivery vehicles (monomeric siRNA (100 nM siRNA), monomeric siRNA/lipofectamine complexes (equivalent to 100 nM siRNA), RNA transcript (12 μg/mL), or RNAtr nanoparticles (19.3 μg/mL)), in which 5 μM CpG oligodeoxynucleotide is used as a positive control for INF-α, 50 ng/mL lipopolysaccharide is used as a positive control for TNF-α, FIGS. 3e and 3f show fluorescence microscopic images and flow cytometry results of folate receptor-negative A549 human lung adenocarcinoma cells and folate receptor-positive SKOV3 human ovarian carcinoma cells at 48 hours after treatment of the cells with FAM-labeled RNAtr nanoparticle (final concentration of 10 μg/mL), and FIG. 3g shows flow cytometry results of SKOV3 cells at 48 hours after treatment of the cells with non-folate-conjugated RNA transcript labeled with fluorescence;

FIG. 4a shows fluorescence microscopic images and flow cytometry results of RFP fluorescent protein-expressing SKOV3 cells at 48 hours after treatment of the cells with anti-RFP siRNA sequence-containing RNAtr nanoparticle, and also fluorescence microscopic images and flow cytometry results of SKOV3-RFP cells after treatment of the cells with PBS buffer as a control group, FIGS. 4b and 4c show the results of Western blotting using anti-RFP antibodies, in which RFP fluorescent proteins were quantified over time after treatment of SKOV3-RFP cells with RNA transcript and RNAtr nanoparticle, respectively and the results of FIG. 4c are presented as mean±standard deviation (n=3), $*p<0.05$ by one-way ANOVA with Tukey's multiple comparison test, FIG. 4d shows the results of quantitative reverse transcription PCR (qRT-PCR) for quantifying the amounts of RFP mRNA over time in SKOV3-RFP cells treated with RNAtr nanoparticle, FIG. 4e shows the results of qRT-PCR for quantifying the amounts of RFP mRNA in SKOV3-RFP cells treated with monomeric anti-RFP siRNA, monomeric anti-RFP siRNA/lipofectamine complexes and RNAtr nanoparticle by varying siRNA concentration, respectively, in which the numbers in brackets represent siRNA concentrations expected to be generated from RNAtr nanoparticles by intracellular Dicer, and the results of FIGS. 4d and 4e are presented as mean±standard deviation (n=3 for one of three independent experiments), $*p<0.05$, $p<0.005$, $*p<0.001$ by one-way ANOVA with Tukey's multiple comparison test, as compared to the control;

FIG. 5a shows biodistribution over time after intravenous injection (2 mg/kg, 200 μL per mouse; 4 mice) of Cy5-labeled RNAtr nanoparticles to SKOV3 xenograft mouse models, FIG. 5b shows the results of measuring fluorescence intensity of RNAtr nanoparticles accumulated in cancer tissues over time, FIG. 5c shows fluorescence intensity images of RNAtr nanoparticles accumulated in cancer tissues and organs that were excised at 2 days after intravenous injection of fluorescence-labeled RNAtr nanoparticles, FIG. 5d shows the results of single intravenous injection (I.V.) of 50 μg of RNAtr nanoparticle and double intravenous injection (I.V.) of 25 μg of RNAtr nanoparticle, in which the injections were conducted when strong RFP intensity was detected in SKOV3-RFP xenograft mice prepared by injecting RFP fluorescent protein-expressing SKOV3 tumor cells (SKOV3-RFP) into the thigh of the mice so as to have cancer tissue of 80 mm$^3$, FIGS. 5d and 5e show that the strong RFP intensity in fluorescence imaging was observed before intravenous injection, but the intensity was remarkably reduced after 2 days, and no reduction in RFP intensity was observed in fluorescence imaging of cancer tissues over time after single intravenous injection of PBS buffer or 50 μg of RNA transcript as a control group, FIG. 5f shows fluorescence intensity images (left) of cancer tissues excised from mice at 2 days after treatment of FIG. 5d, and the results of qRNT-PCR for quantifying RFP mRNA remaining in cancer tissues, in which the results of FIG. 5f are presented as mean±standard deviation (n=3), *p<0.001 by one-way ANOVA with Tukey's multiple comparison test, as compared to the PBS control;

FIG. 6a shows that a ratio of folate to DNA is 0.95±0.2, in which absorbance of folate and DNA was measured at 260 and 363 nm to obtain a standard curve thereof and absorbance coefficient thereof was calculated in order to measure a ratio of folate to DNA (folate-to-DNA ratio) in the folate-DNA conjugate, FIG. 6b shows the results of 3% agarose gel electrophoresis, in which a band is observed when RNA transcript, DNA-Chol, and FA-DNA form complementary paring as a bar indicated, FIG. 6c shows the results of measuring zeta potentials of RNA transcript and RNAtr nanoparticle using DLS, FIG. 6d shows a Debye plot for measuring the amount of RNA transcript molecules using static light scattering (SLS), in which the amount of RNA transcript molecules was 1000±387 kDa, and the amount of RNAtr nanoparticle molecules calculated therefrom was 1400±541.8 kDa, and FIG. 6e shows the results of MTT assay for measuring cytotoxicity according to RNAtr nanoparticle concentration in SKOV3 cells, in which about 90% or more of SKOV3 cells showed no cell death until the RNAtr nanoparticle concentration reached 50 μg/mL;

FIG. 7 shows the results of quantifying the electrophoresis results which were measured in FIG. 3b (the results are presented as mean±standard deviation (n=3), *p<0.001 by one-way ANOVA); and FIG. 8 shows the results of in vivo gene silencing observed in three mice per each administration group in the experiment of FIG. 5d.

DETAILED DESCRIPTION OF THE EMBODIMENTS

Hereafter, the present invention will be described in more detail in light of the following Examples. However, these Examples are for illustrative purposes only, and the invention is not intended to be limited by these Examples.

Example 1. Preparation of RNA/DNA Nanoparticle for siRNA Delivery 1-1. Design of RNA/DNA Nanoparticle for siRNA Delivery The present inventors designed a linear DNA sequence (SEQ ID NO. 1), of which both ends are complementary to a T7 promoter sequence (SEQ ID NO. 4), and they also designed an RNA transcript (SEQ ID NO. 5) to be produced from DNA of SEQ ID NO. 1 as a template, in which the RNA transcript has sequences complementary to a DNA-Chol conjugate (SEQ ID NO. 2) and a folate-DNA conjugate (SEQ ID NO. 3) so as to form RNA/DNA base-pairing.

A two-dimensional structure of RNA was analyzed by RNA mfold program (http://mfold.rna.albany.edu/?q=mfold/RNA-Folding-Form), and as shown in FIG. 1, numerous repeats of a hairpin structure containing siRNA sequence were observed. In this Example, a generation process of RNA/DNA nanoparticles for siRNA delivery is shown in FIG. 1b.

1-2. Preparation of RNA/DNA Nanoparticle for siRNA Delivery by RCT and RNA/DNA Hybridization To prepare the RNA/DNA nanoparticle for siRNA delivery which was designed in Example 1-1, the linear DNA (SEQ ID NO. 1) and T7 promoter primer (SEQ ID NO. 4) were mixed at a molar ratio of 1:1, and then denatured at 95° C. for 2 minutes and cooled to 25° C. so as to prepare an open circular DNA/T7 promoter hybrid, in which the linear DNA and T7 promoter primer were annealed (see FIG. 1). T4 DNA ligase and 5 mM ATP were added to this circular DNA/T7 promoter hybrid, and allowed to react at 16° C. for 12 hours so as to prepare a closed circular DNA/T7 promoter hybrid by sealing the nick. To this hybrid, T7 RNA polymerase (5 U/μL), a reaction buffer (4 mM Tris-HCl, 0.6 mM MgCl$_2$, 1 mM DTT, 0.2 mM spermidine), rNTP (2 mM, ribonucleotide solution mix, NEB), and an RNase inhibitor (1 U/μL) were added, and rolling circle transcription (RCT) was allowed at 37° C. for 1 hour to prepare a polymerized RNA transcript. To terminate the RCT reaction, DNase 1 (2 U/μL) was reacted therewith at 15° C. for 15 minutes, and then 0.2 M EDTA was added thereto, followed by heat treatment at 90° C. for 5 minutes.

The RNA transcript and a DNA-Chol conjugate were mixed at a weight ratio of 1:0.2 in a hybridization buffer (30 mM Tris-HCl (pH 7.8), 10 mM MgCl$_2$, 10 mM DTT), and then denatured at 65° C. for 5 minutes and cooled at 4° C. for 2 hours so as to prepare an RNA transcript/DNA-Chol (RNAtr/DNA-Chol) hybrid. This hybrid and a folate-DNA conjugate were mixed at a ratio of RNA transcript:DNA-Chol:FA-DNA=1:0.2:0.2 (w/w/w), and MgCl$_2$ was further added to be 10 mM, and left at room temperature for 2 hours so as to obtain an RNAtr/DNA-Chol/FA-DNA hybrid (see FIG. 1).

As shown in FIG. 2b, the melting temperature of RNAtr/DNA-Chol hybrid and RNAtr/FA-DNA hybrid was 44° C., and the melting temperature of RNAtr/DNA-Chol/FA-DNA hybrid was 57° C., indicating that RNA/DNA duplex is disassembled into individual strands, and thus the RNAtr nanoparticle is prepared resulting from RNA/DNA hybridization.

For reference, the folate-DNA conjugate may be prepared by the following method. 10 mM 5'-amine-modified DNA was dissolved in a conjugation buffer (100 mM MES, 500 mM NaCl, pH 6.0), and then mixed with Sulfo-NHS (10 mM) and EDC (4 mM) solution. Excessive 10 mole times of folate was added to the mixture, and allowed to react at 22° C. for 3 hours to prepare a folate-DNA conjugate, in which a carboxylate group of folate binds to 5'-amine group of DNA. To inactivate unreacted EDC after termination of the reaction, mercaptoethanol was added. Only folate-DNA conjugate was purified using an amicon ultra-centrifugal filter (3K MWCO, Millipore). A ratio of the bound folate was measured as 0.95±0.2 per DNA, as shown in FIG. 6a.

Example 2. Characterization of RNA/DNA Nanoparticle for siRNA Delivery

The RNA transcript, RNAtr/DNA-Chol hybrid, and RNAtr/DNA-Chol/FA-DNA hybrid prepared in Example 1-1 were electrophoresed on a 3% agarose gel (FIGS. 2a and 6b). The RNA transcript exhibited a wide molecular weight distribution, whereas the RNAtr/DNA-Chol hybrid (1:0.2, w/w) did not move from the well to the bottom while forming large particles. In particular, the results of electrophoresis showed that the size of the RNAtr/DNA-Chol hybrid (1:0.1, w/w) is placed between the RNA transcript and the RNAtr/DNA-Chol hybrid (1:0.2, w/w). FIGS. 2c, 2d and 6c show the particle size and zeta potential measured using dynamic light scattering (DLS).

The RNA transcript formed microparticles of 1 μm or larger, but the RNAtr/DNA-Chol hybrid (1:0.2, w/w) formed nanoparticles of 120 nm resulting from self-assembly. The RNAtr/DNA-Chol hybrid (1:0.1, w/w) showed a particle size of 357 nm and two size distributions in size distribution analysis by DLS, suggesting that RNA/DNA hybridization did not sufficiently occur due to lack of DNA-Chol. The size of RNAtr/DNA-Chol/FA-DNA hybrid was about 190 nm. In particular, the RNA transcript and the RNAtr/DNA-Chol/FA-DNA (1:0.2:0.2, w/w/w) showed zeta potential of −11.9±2.1 mV and −1.5±3.3 mV, respectively, which is understood to be attributed to a counterbalancing effect of magnesium ions remaining in the solution, because more magnesium ions bind to highly condensed RNAtr/DNA-Chol/FA-DNA hybrid.

As shown in TEM image analysis of FIG. 2e, the RNA transcript, RNAtr/DNA-Chol, and RNAtr/DNA-Chol/FA-DNA formed spherical particles and showed a particle size similar to the result of DLS. These results indicate that the micrometer-sized RNA transcripts form nanometer-sized nanoparticles by hybridization with the DNA-Chol conjugate and the folate-DNA conjugate, and also suggest that highly condensed RNA/DNA nanoparticles can be prepared without using cationic polymers which may cause the cytotoxicity problem.

Example 3. Stability Test of RNA/DNA Nanoparticle for siRNA Delivery

In order to examine stability of RNA/DNA nanoparticle for siRNA delivery in the blood, degradation products obtained under 30% FBS conditions over time were analyzed by electrophoresis. First, monomeric siRNA as a control group was completely degraded within 1 hour and about 80% or more of the RNA transcript was degraded after 6 hours, whereas about 65% of the RNAtr nanoparticle remained intact even after 24 hours, indicating very excellent stability against nuclease. It is understood that siRNAs located inside the RNA/DNA nanoparticle are physically protected from nuclease attacks, and in particular, folate exposed to the outside considerably blocks access of nuclease.

To examine stability against a large amount of macroanionic molecules in extracellular matrix located outside of the plasma membrane, stability of the RNAtr nanoparticle was examined under heparin condition (FIGS. 3b and 7). It was observed that when heparin was mixed with monomeric siRNA/PEI complexes as a control group, siRNA was easily dissociated from PEI, but RNAtr nanoparticles did not show disassembly of the particle under excessive heparin conditions. These results suggest that the existing siRNA vehicles have low delivery efficiency because the vehicles are loaded with siRNAs by charge-charge interactions and thus siRNAs are easily dissociated due to macroanionic molecules around the cell membrane, whereas the RNA/DNA nanoparticles of the present invention deliver siRNA without charge-charge interaction and thus are not hindered by macroanionic molecules around the cell membrane.

After cell penetration, the RNAtr nanoparticles generate siRNAs by intracellular Dicer enzyme. Thus, it was intended to examine generation of siRNA by Dicer in vitro. 4 μg of the RNA transcript generated 0.84 μg of siRNA at 1 hour after reaction, whereas 4 μg of RNAtr nanoparticle generated 0.52 μg of siRNA at 6 hours after reaction, which correspond to about 61% of the theoretical amount of siRNA produced by the RNA transcript, and about 53.1% of the theoretical amount of siRNA produced by the RNAtr nanoparticle, respectively.

In order to examine innate immunogenicity which may be caused by siRNA or siRNA vehicle, INF-α and TNF-α inductions were examined in human PBMC cells (FIG. 3d). Compared to CpG oligodeoxynucleotide causing INF-α induction, the RNAtr nanoparticle and the RNA transcript did not cause INF-α induction. Interestingly, monomeric siRNA/lipofectamine complexes induced considerably high levels of INF-α, and RNAtr nanoparticles did not stimulate innate immunogenicity, compared to the known lipofectamine. When TNF-α induction was examined, lipopolysaccharides induced considerably high levels of TNF-α, whereas the RNAtr nanoparticle and the RNA transcript hardly caused TNF-α induction. These results suggest that the RNAtr nanoparticles do not stimulate innate immunogenicity, and therefore, their intravenous injection is possible upon clinical applications.

As shown in FIG. 6e, MTT assay was carried out to examine intracellular biocompatibility (Choi, Y. H.; Liu, F.; Kim, J. S.; Choi, Y. K.; Park, J. S.; Kim, S. W. J. Control. Rel. 1998, 54, 39-48.). In detail, SKOV3 cells in the exponential growth phase were cultured in a 96-well plate at a density of 20,000 cells/well, and then each well was treated with the RNA/DNA nanoparticle for siRNA delivery prepared in Example 1-2 by varying its concentration, followed by incubation for 24 hours. 200 uL of MTT solution (0.5 mg/mL) was added to each well, and allowed to react for 4 hours. Then, 200 uL of DMSO was added thereto and allowed to react for 10 minutes, and measured at 570 nm by ELISA. As shown in FIG. 6e, the RNA/DNA nanoparticle for siRNA delivery showed excellent biocompatibility until the concentration of 50 μg/mL.

Example 4. Cancer Cell-Targeting Test of RNA/DNA Nanoparticle for siRNA Delivery In order to examine target specificity for folate receptor, folate receptor-positive SKOV3 tumor cells and folate receptor-negative A549 adenocarcinoma cells were treated with fluorescence-labeled RNAtr nanoparticles. 3 hours later, fluorescence microscopy and flow cytometry were conducted (FIGS. 3e and 3f). A large amount of the RNAtr nanoparticles permeated SKOV3 cells, but did not A549 cells. The result of flow cytometry showed that about 80% of RNAtr nanoparticles permeated SKOV3 cells, but none of them permeated A549 cells at 3 hours after treatment. When folate receptors were saturated by pre-treatment of folate, only about 30% of RNAtr nanoparticles permeated SKOV3 cells (FIG. 3f). These results indicate that selective binding of the RNAtr nanoparticles to the cells occurs by folate.

When SKOV3 cells were treated with the RNA transcript, no binding was observed, which is understood to be attributed to absence of folate (FIG. 3g).

Example 5. Gene Silencing Test of RNA/DNA Nanoparticle for siRNA Delivery

SKOV3 cells (SKOV3-RFP) expressing RFP fluorescent proteins were treated with RNAtr nanoparticles containing an anti-RFP siRNA sequence (final concentration of 10 μg/mL). 48 hours later, a reduction in RFP fluorescence intensity was examined under a fluorescence microscope. SKOV3-RFP treated with PBS buffer as a control group showed no reduction in RFP fluorescence intensity, whereas the cells treated with RNAtr nanoparticles showed a great reduction in fluorescence intensity (FIG. 4a). Further, the result of flow cytometry showed about 50% reduction in fluorescence intensity.

As shown in FIGS. 4b and 4c, when suppression of gene expression was examined using RFP antibodies, no reduction in RFP proteins was observed in SKOV3-RFP cells treated with RNA transcript, whereas about 45% reduction in RFP proteins was observed in SKOV3-RFP cells treated with RNAtr nanoparticle after 48 hours.

Further, the present inventors examined siRNA delivery effect of the RNA/DNA nanoparticle for siRNA delivery by quantifying intracellular RFP mRNA using qRT-PCR. qRT-PCR was performed using primers for RFP mRNA (forward primer 5'-GCGTGATGAACTTCGAGGA-3' (SEQ ID NO. 6) and reverse primer 5-GATGAAGCAGCCGTCCTG-3' (SEQ ID NO. 7)) and primers for β-actin as a control (forward primer 5'-AGAGGGAAATCGTGCGTGAC-3' (SEQ ID NO. 8) and reverse primer 5'-CAATAGTGAT-GACCTGGCCGT-3' (SEQ ID NO. 9) to quantify the amount of intracellular RFP mRNA (denaturation at 95° C./30 sec, annealing at 51° C./30 sec, elongation at 72° C./30 sec, 20 cycles). After electrophoresis, quantification of each band was performed using a DNR's GelQuant (image analysis) program and the results are shown in FIG. 4d. A reduction in the amount of RFP mRNA was observed at 24 hours after treatment of the RNAtr nanoparticle, and the amount of RFP mRNA was reduced to about 30% after 48 hours.

Gene silencing effects of RNAtr nanoparticle and siRNA/lipofectamine which generate the same amount of siRNA were compared by qRT-PCR (FIG. 4e). The RNAtr nanoparticle corresponding to 20 nM siRNA reduced a remarkable amount of RFP mRNA, but siRNA/lipofectamine did not. The RNAtr nanoparticle having a concentration of siRNA as high as 50 nM exhibited excellent gene silencing effect, compared to siRNA/lipofectamine.

Example 6. Test of Cancer-Specific Accumulation of RNA/DNA Nanoparticle for siRNA Delivery in Mouse Xenograft Model SKOV3 cancer cells ($1 \times 10^7$) were injected to the left thigh of 5-week-old female BALB/c nude mouse, and then left until the cancer tissue grew to a volume of about 80 $mm^3$. After intravenous injection of fluorescence-labeled Cy5-RNAtr nanoparticles (50 μg) via the tail vein of the mouse, biodistribution of fluorescence-labeled nanoparticles was examined in predetermined time intervals for 48 hours by IVIS spectrum (Caliper Life Science Inc., USA) (FIGS. 5a and 5b). 1 hour after intravenous injection, fluorescence of nanoparticles accumulated in the cancer tissue was clearly detected, and the maximum fluorescence intensity was observed in the cancer tissue at 2 hours after injection, and the fluorescence was maintained until about 48 hours. These results showed that the RNAtr nanoparticles intravenously injected were selectively accumulated in cancer tissues, but not clearly accumulated in the live or thymus, in which accumulation of polymer nanoparticles are frequently found. At 48 hours after intravenous injection, the cancer tissues and organs were excised from the mice at autopsy, and fluorescence intensity was measured. Highest accumulation of nanoparticles was observed in the cancer tissues, which is consistent with the result of FIG. 5a (FIG. 5c).

Example 7. Test of Gene Silencing of RNA/DNA Nanoparticle for siRNA Delivery in Mouse Xenograft Model SKOV3-RFP cancer cells ($1 \times 10^7$) expressing RFP fluorescent protein were injected to the left thigh of 5-week-old female BALB/c nude mouse so as to prepare a mouse model, in which the cancer tissue grew to a size of 5-7 mm to show a strong RFP fluorescence intensity. Single intravenous injection of 50 μg of RNAtr nanoparticle or double intravenous injection of 25 μg of RNAtr nanoparticle in a one-day interval was performed, and then changes in RFP fluorescence intensity was examined in the cancer tissue for a predetermined time by IVIS spectrum (FIGS. 5d, 5e and 8). As a control group, PBS buffer or RNA transcript was intravenously injected to mice. 2 days later, about 80% reduction in RFP fluorescence intensity was observed in the mice by single injection of RNAtr nanoparticles, and about 45% reduction in RFP fluorescence intensity was observed in the mice by double injection of RNAtr nanoparticles. In contrast, RFP fluorescence intensity was increased in the control mouse. 2 days after intravenous injection, the cancer tissues were excised from the mice, and fluorescence intensity was measured. Strong fluorescence signals were observed in the cancer tissue of the control mouse, whereas much weaker RFP fluorescence signals were observed in the mice treated with RNAtr nanoparticles (FIG. 5f). When RFP mRNA remaining in the excised cancer tissues were quantified by qRT-PCR, a relatively great reduction in the amount of RFP mRNA was observed only in the cancer tissues treated with RNAtr nanoparticles.

What is claimed is:

1. An amphiphilic RNA/DNA nanoparticle for delivering siRNA, comprising
   a RNA transcript comprising a repeating unit including a sense sequence of a siRNA to be delivered, a first RNA sequence, an antisense sequence of a siRNA to be delivered, and a second RNA sequence at the direction of 5'-terminus to 3'-terminus, wherein the sense sequence, the antisense sequence of the siRNA to be delivered, the first and the second RNA sequence are comprised of 5 to 50 bases,
   a first DNA sequence-cholesterol conjugate including a first DNA sequence being capable of binding complementarily to the first RNA sequence and cholesterol connected to 3'-terminus of the first DNA sequence, wherein the first DNA sequence is SEQ ID NO:2, and
   a second DNA sequence-ligand conjugate including a second DNA sequence being capable of binding complementarily to the second RNA sequence and a target-specific ligand connected to 5'-terminus of the second DNA sequence.

2. The amphiphilic RNA/DNA nanoparticle according to claim 1, wherein the repeating unit of RNA transcript further comprises a sequence connected to either 5'-terminus or 3'-terminus which is capable of binding complementary to a transcription promoter.

3. The amphiphilic RNA/DNA nanoparticle according to claim 1, wherein the repeating unit is comprised at a repeating number of 1 to 1,000,000.

4. The amphiphilic RNA/DNA nanoparticle according to claim 1, wherein the target-specific ligand is target-directed compounds, target-directed peptides, target-directed antibodies, or target-directed aptamers.

5. The amphiphilic RNA/DNA nanoparticle according to claim 4, wherein the target-specific ligand is a folate or RGD (Arg-Gly-Asp) peptide.

6. The amphiphilic RNA/DNA nanoparticle according to claim 1, wherein the diameter of nanoparticle is 150 nm to 450 nm.

7. The amphiphilic RNA/DNA nanoparticle according to claim 1, wherein the second DNA sequence-ligand conjugate is the second DNA sequence-folate conjugate.

8. A target-directed vehicle used for delivering siRNA, comprising a nanoparticle of claim 1.

* * * * *